(12) United States Patent
Shinoda et al.

(10) Patent No.: US 11,625,830 B2
(45) Date of Patent: Apr. 11, 2023

(54) INFORMATION PROCESSING APPARATUS, INFORMATION PROCESSING METHOD, PROGRAM, AND OBSERVATION SYSTEM

(71) Applicant: Sony Corporation, Tokyo (JP)

(72) Inventors: Masataka Shinoda, Kanagawa (JP); Takeshi Ohashi, Kanagawa (JP)

(73) Assignee: Sony Corporation, Tokyo (JP)

( * ) Notice: Subject to any disclaimer, the term of this patent is extended or adjusted under 35 U.S.C. 154(b) by 630 days.

(21) Appl. No.: 16/628,448

(22) PCT Filed: Jul. 4, 2018

(86) PCT No.: PCT/JP2018/025333
§ 371 (c)(1),
(2) Date: Jan. 3, 2020

(87) PCT Pub. No.: WO2019/013064
PCT Pub. Date: Jan. 17, 2019

(65) Prior Publication Data
US 2020/0126233 A1    Apr. 23, 2020

(30) Foreign Application Priority Data

Jul. 10, 2017    (JP) .............................. JP2017-135067

(51) Int. Cl.
*G06K 9/00*    (2022.01)
*G06T 7/00*    (2017.01)
(Continued)

(52) U.S. Cl.
CPC .............. *G06T 7/0016* (2013.01); *G06T 7/20* (2013.01); *G06T 7/70* (2017.01);
(Continued)

(58) Field of Classification Search
CPC ........... G06T 7/0016; G06T 7/20; G06T 7/70; G06T 2207/10016; G06T 2207/20076;
(Continued)

(56) References Cited

U.S. PATENT DOCUMENTS 7,110,584 B2 * 9/2006 Onami ...................... G06T 7/11
382/128
2003/0108230 A1 * 6/2003 Miyano ................ G06V 20/695
382/173
(Continued)

FOREIGN PATENT DOCUMENTS

EP    1 267 305 A1    12/2002
JP    2001311730 A    11/2001
JP    2011-192109 A    9/2011

OTHER PUBLICATIONS

Kheradmand Shakiba et al: "Human blastocyst segmentation using neural network", 2016 IEEE Canadian Conference on Electrical and Computer Engineering (CCECE), IEEE, May 15, 2016 (May 15, 2016), pp. 1-4, XP032989003, DOI: 10.1109/CCECE.2016.7726763 [retrieved on Oct. 31, 2016].

(Continued)

*Primary Examiner* — Tom Y Lu
(74) *Attorney, Agent, or Firm* — Wolf, Greenfield & Sacks, P.C.

(57) ABSTRACT

There is provided an information processing apparatus, including: an image obtaining unit configured to obtain a plurality of images of a fertile ovum captured in time series; a recognizing unit including a probability image generating unit configured to generate, for each image of the fertile ovum, a probability image, wherein each position in the probability image represents the probability that at least part of the fertile ovum is present at the corresponding position in the image of the fertile ovum; and a feature amount calculating unit configured to calculate time-series transfor- (Continued)

mation of the fertile ovum from the probability images over the time series, and calculate a feature amount of the fertile ovum based on the transformation.

33 Claims, 30 Drawing Sheets

(51) Int. Cl.
    *G06T 7/70*     (2017.01)
    *G06T 7/20*     (2017.01)

(52) U.S. Cl.
    CPC ............ *G06T 2207/10016* (2013.01); *G06T 2207/20076* (2013.01); *G06T 2207/20224* (2013.01); *G06T 2207/30044* (2013.01)

(58) Field of Classification Search
    CPC . G06T 2207/20224; G06T 2207/30044; G06T 7/0012; G06V 20/69; C12M 41/46
    See application file for complete search history.

(56) References Cited

U.S. PATENT DOCUMENTS

| | | | |
|---|---|---|---|
| 2010/0040276 A1* | 2/2010 | Zerfass | G06V 20/695 382/133 |
| 2015/0268227 A1* | 9/2015 | Tan | G06T 7/0016 435/29 |

OTHER PUBLICATIONS

Rad, Reza Moradi et al: Coarse-to-fine texture analysis for inner cell mass identificaton in human blastocyst microscopic images, 2017 Seventh International Conference on Image Processing Theory, Tools and Applications (IPTA), IEEE, Nov. 28, 2017 (Nov. 28, 2017), pp. 1-5. XP033328282. DOI: 10.1109/IPTA.2017.8310152 [retrieved on Mar. 8, 2018].

International Search Report and Written Opinion dated Dec. 6, 2018 in connection with International Application No. PCT/JP2018/025333.

Filho et al., A review on automatic analysis of human embryo microscope images. Open Biomedical Engineering Journal. 2010;4:170-7. DOI: 10.2174/1874120701004010170.

Iwata et al., Observation of human embryonic behavior in vitro by high-resolution time-lapse cinematography. Reproductive Medicine and Biology. 2016;15(3):145-154. DOI: 10.1007/S12522-015-0231-7.

Khan et al., Automated Monitoring of human embryonic cells up to the 5-cell stage in time-lapse microscopy images. IEEE 12th International Symposium on Biomedical Imaging (ISBI). 2015, pp. 389-393. DOI: 10.1109/ISBI.2015.7163894.

Moriwaki et al., Embryo evaluation by analyzing blastomere nuclei. Human Reproduction. 2004;19(1):152-156. DOI: 10.1093/humrep/deh003.

* cited by examiner (a)
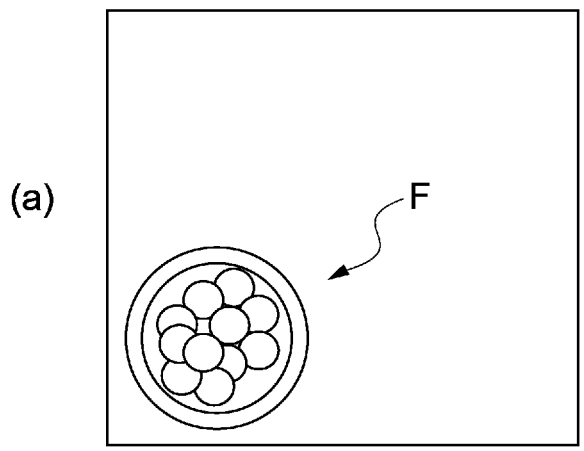
Sixteen-cell stage
(b)
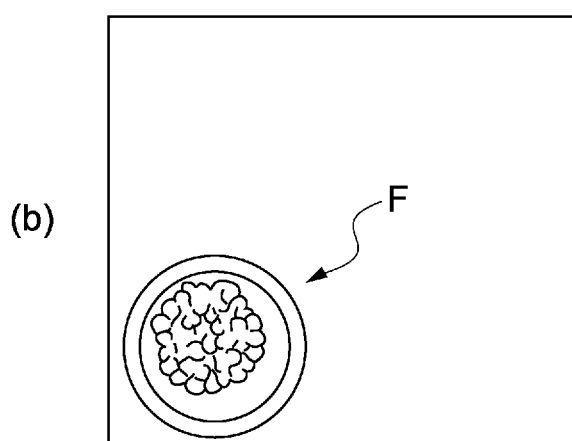
Morula stage
FIG.13

(a)
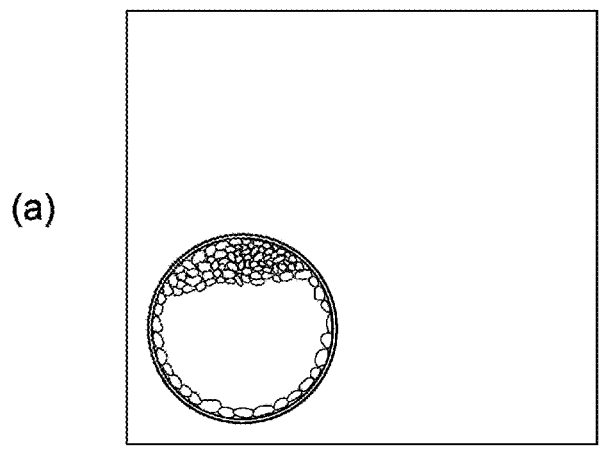
Blastocyst stage
(b)
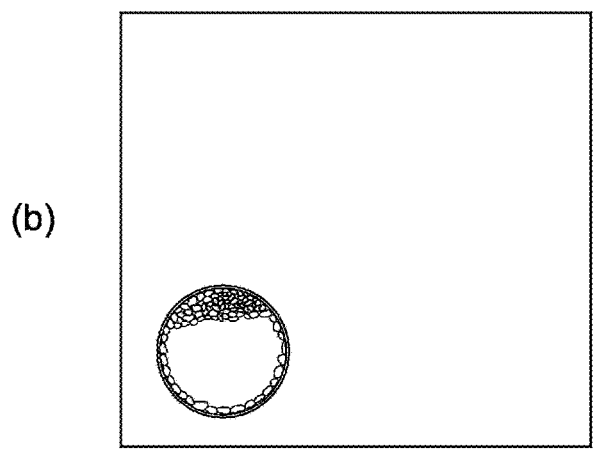
Case where blastocyst and zona pellucida contract
(c)
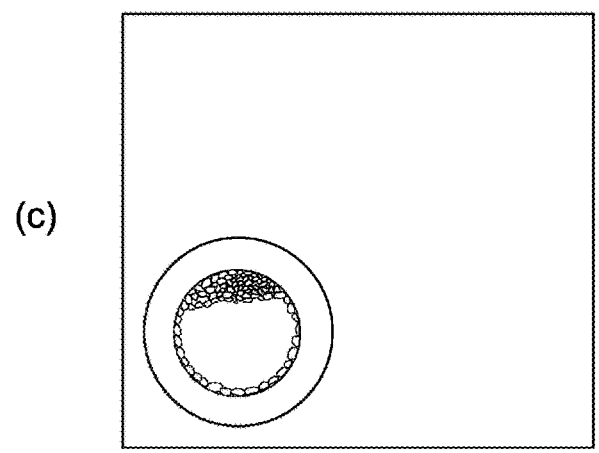
Case where only blastocyst contracts
FIG.15

INFORMATION PROCESSING APPARATUS, INFORMATION PROCESSING METHOD, PROGRAM, AND OBSERVATION SYSTEM

CROSS REFERENCE TO RELATED APPLICATIONS

This application claims the benefit under 35 U.S.C. § 371 as a U.S. National Stage Entry of International Application No. PCT/JP2018/025333, filed in the Japanese Patent Office as a Receiving Office on Jul. 4, 2018, which claims priority to Japanese Patent Application Number JP2017-135067, filed in the Japanese Patent Office on Jul. 10, 2017, each of which is hereby incorporated by reference in its entirety.

TECHNICAL FIELD

The present technique relates to an information processing apparatus, an information processing method, a program, and an observation system applicable to evaluation of a cell or the like.

BACKGROUND ART

According to Patent Literature 1, a reference image is selected from an image group, which includes captured images of a plurality of fertile ova, and the profile of the fertile ovum of the selected reference image is detected as a reference profile. A predetermined profile processing is executed with reference to the reference profile, and the profile of the fertile ovum of an arbitrary image of the image group is therefore determined. As a result, the positions of the fertile ovum of all the images of the image group are matched accurately, and therefore it is possible to output such fertile ovum images. The accuracy of analysis of a fertile ovum may be therefore increased.

CITATION LIST

Patent Literature

PTL 1: Japanese Patent Application Laid-open No. 2011-192109

SUMMARY

Technical Problem

It is desirable to help improve the evaluation of a fertile ovum under observation or the like.

In view of the above-mentioned circumstances, it is desirable to provide an information processing apparatus, an information processing method, a program, and an observation system with which a fertile ovum under observation can be evaluated with a high degree of accuracy.

Solution to Problem

According to an embodiment of the present technique, there is provided an information processing apparatus, including: an image obtaining unit configured to obtain a plurality of images of a fertile ovum captured in time series; a recognizing unit including a probability image generating unit configured to generate, for each image of the fertile ovum, a probability image, wherein each position in the probability image represents the probability that at least part of the fertile ovum is present at the corresponding position in the image of the fertile ovum; and a feature amount calculating unit configured to calculate time-series transformation of the fertile ovum from the probability images over the time series, and calculate a feature amount of the fertile ovum based on the transformation.

According to the above-mentioned technique, the quality of the fertile ovum may be multilaterally evaluated in view of not only morphological findings of the fertile ovum but also time-series transformation of the fertile ovum and the feature amount based on the transformation. The fertile ovum under observation may be evaluated with a high degree of accuracy.

The recognizing unit may further include a binarized image generating unit configured to generate a plurality of binarized images from a plurality of the probability images by processing the probability images by means of a binarizing process with a predetermined threshold value for each pixel, and is further configured to recognize the fertile ovum on the basis of the binarized images, and the feature amount calculating unit is further configured to calculate the time-series transformation of the fertile ovum from the binarized images, and calculate the feature amount of the fertile ovum based on the transformation.

The recognizing unit may further include an overlay image generating unit configured to generates overlay images by overlaying the binarized images and the images of the fertile ovum, and is further configured to recognize the fertile ovum on the basis of the overlay images, and the feature amount calculating unit is further configured to calculate the time-series transformation of the fertile ovum from the overlay images, and calculate the feature amount of the fertile ovum based on the transformation.

The recognizing unit may be further configured to recognize a zona pellucida of the fertile ovum and a cell in the fertile ovum.

The feature amount calculating unit may be further configured to calculate, as the transformation, change of an area of the zona pellucida and change of an area of the cell in the fertile ovum.

Therefore, a user may quantitatively and objectively know the contraction/dilation activity of a zona pellucida and cells in the fertile ovum.

The feature amount calculating unit may be further configured to calculate, as the feature amount, at least one of compaction time of the fertile ovum and cleavage time of the fertile ovum on the basis of time-series change of the area of the zona pellucida and time-series change of the area of the cell in the fertile ovum.

Therefore, for example, a user may quantitatively and objectively know the compaction time or cleavage time in a process in which the fertile ovum grows from a sixteen-cell stage to a morula stage. This improves the accuracy of the evaluation of the fertile ovum.

The recognizing unit may be further configured to recognize a blastocyst as the cell in the fertile ovum.

The feature amount calculating unit may be further configured to calculate, as the feature amount, at least one of a number of times of contraction, a contraction diameter, contraction speed, a contraction time period, contraction intervals, contraction strength, contraction frequency, a number of times of dilation, a dilation diameter, a dilation speed, a dilation time period, dilation intervals, dilation strength, and dilation frequency of the zona pellucida and the blastocyst on the basis of time-series change of a difference between the area of the zona pellucida and an area of the blastocyst.

Therefore, a user may quantitatively and objectively know minute contraction/dilation activity of a zona pellucida and a blastocyst. This improves the accuracy of the evaluation of the fertile ovum.

The recognizing unit may be further configured to recognize a zona pellucida of the fertile ovum.

The feature amount calculating unit may be further configured to calculate, as the transformation, a change of a physiological characteristic of the zona pellucida. The may be, for example, at least one of a diameter, an area, and a thickness of the zona pellucida.

Therefore, a user may confirm the start time of the change of the state of the fertile ovum, the growing speed, and the like. The user may know quantitatively and objectively know the contraction/dilation activity of the fertile ovum in time series. This improves the accuracy of the evaluation of the fertile ovum.

The recognizing unit may be further configured to recognize a pronucleus of the fertile ovum.

The feature amount calculating unit may be further configured to calculate, as the transformation, a change of an area of the pronucleus.

Therefore, it is possible to determine appearance time and disappearance time of the pronucleus in the growth process of the fertile ovum. This improves the accuracy of the evaluation of the fertile ovum.

The feature amount calculating unit may be further configured to calculate, as the feature amount, a number of pronuclei on the basis of the area of the pronucleus.

Therefore, it is possible to determine whether or not the pronucleus of the fertile ovum is abnormal on the basis of the number of pronuclei. In other words, it is possible to determine whether or not the fertile ovum is normally fertilized, and further determine the type of abnormal fertilization.

The recognizing unit may be further configured to recognize a first polar body and a second polar body of the fertile ovum.

The feature amount calculating unit may be further configured to calculate, as the feature amount, a number of polar bodies of the fertile ovum on the basis of a difference between a sum of an area of the first polar body and an area of the second polar body and the area of the first polar body.

Therefore, it is possible to determine whether or not a second polar body is produced from the fertile ovum after fertilization on the basis of the number of polar bodies of the fertile ovum. In other words, it is possible to determine whether or not the fertile ovum is normally fertilized.

The recognizing unit may be further configured to recognize a nucleus of a blastomere of the fertile ovum.

The feature amount calculating unit may be further configured to calculate, as the feature amount, a number of nuclei on the basis of an area of the nucleus.

Therefore, it is possible to determine whether or not the fertile ovum is in a polynuclear state. When a fertile ovum is in a polynuclear state, the fertile ovum usually fails. In particular, the the fertile ovum in the polynuclear state usually results in a failed incubation or deformed fetus. Accordingly, by identifying a fertile ovum in a polynuclear state, the culture may be stopped.

The recognizing unit may be further configured to recognize a zona pellucida of the fertile ovum, a cell in the fertile ovum, and fragmentation of the fertile ovum.

The feature amount calculating unit may be further configured to calculate, as the feature amount, a proportion of an area of the fragmentation to a sum of an area of the zona pellucida and an area of the cell in the fertile ovum.

The recognizing unit may be further configured to recognize a translucent zone in a peripheral ooplasm of the fertile ovum and a cell in the fertile ovum.

The feature amount calculating unit may be further configured to calculate, as the transformation, change of a proportion of an area of the translucent zone in the peripheral ooplasm to an area of the cell in the fertile ovum.

Therefore, it is possible to determine appearance time and disappearance time of a translucent zone (Halo) in the peripheral ooplasm in the growth process of the fertile ovum. This improves the accuracy of the evaluation of the fertile ovum.

The recognizing unit may be further configured to recognize a cell in the fertile ovum.

The feature amount calculating unit may be further configured to calculate change of a time-series motion amount of the cell in the fertile ovum recognized by the recognizing unit.

Therefore, where the change of the motion amount is visualized in the graph or the like, it is possible to evaluate the motion ability of the inside of the fertile ovum.

The information processing apparatus may further include a determining unit configured to determine quality of the fertile ovum on the basis of the feature amount.

The recognizing unit may be further configured to recognize a first polar body and a second polar body of the fertile ovum.

The feature amount calculating unit may be further configured to calculate, as the feature amount, a number of polar bodies of the fertile ovum on the basis of a difference between a sum of an area of the first polar body and an area of the second polar body and the area of the first polar body.

The determining unit may be further configured to determine whether or not the polar bodies of the fertile ovum are abnormal on the basis of the number of polar bodies.

Therefore, not only whether or not the fertile ovum is normally fertilized but also the type of abnormal fertilization are automatically determined.

The recognizing unit may be further configured to recognize a nucleus of a blastomere of the fertile ovum.

The feature amount calculating unit may be further configured to calculate, as the feature amount, a number of nuclei on the basis of an area of the nucleus.

The determining unit may be further configured to determine whether or not the fertile ovum is in a polynuclear state on the basis of the number of nuclei.

Therefore, whether or not the inside of blastomeres of the fertile ovum is in a polynuclear state is automatically determined.

The determining unit may be further configured to determine a growth state of the fertile ovum on the basis of the transformation.

The recognizing unit may be further configured to recognize a zona pellucida of the fertile ovum.

The feature amount calculating unit may be further configured to calculate, as the transformation, change of a thickness of the zona pellucida.

The determining unit may be further configured to determine that the fertile ovum is an expanding blastocyst on the basis of the change of the thickness of the zona pellucida.

The recognizing unit may be further configured to recognize a zona pellucida of the fertile ovum.

The feature amount calculating unit may be further configured to calculate, as the transformation, at least one of change of a diameter of the zona pellucida and change of an area of the zona pellucida.

The determining unit may be further configured to determine that the fertile ovum is an expanding blastocyst on the basis of at least one of the change of the diameter of the zona pellucida and the change of the area of the zona pellucida.

The recognizing unit may be further configured to recognize a pronucleus of the fertile ovum.

The feature amount calculating unit may be further configured to calculate, as the transformation, change of an area of the pronucleus.

The determining unit may be further configured to determine appearance and disappearance of the pronucleus in the fertile ovum on the basis of the change of the area of the pronucleus.

Therefore, pronucleus appearance and disappearance of a pronucleus in the growth process of the fertile ovum are automatically determined.

The feature amount calculating unit may be further configured to calculate, as the feature amount, a number of pronuclei on the basis of the area of the pronucleus.

The determining unit may be further configured to determine whether or not the pronucleus of the fertile ovum is abnormal on the basis of the number of pronuclei.

Therefore, not only whether or not the fertile ovum is normally fertilized but also the type of abnormal fertilization are automatically determined.

The recognizing unit may be further configured to recognize a translucent zone in a peripheral ooplasm of the fertile ovum and a cell in the fertile ovum.

The feature amount calculating unit may be further configured to calculate, as the transformation, change of a proportion of an area of the translucent zone in the peripheral ooplasm to an area of the cell in the fertile ovum.

The determining unit may be further configured to determine appearance and disappearance of the translucent zone in the peripheral ooplasm in the fertile ovum on the basis of the change of the proportion.

Therefore, appearance and disappearance of a translucent zone (Halo) in the peripheral ooplasm in the growth process of the fertile ovum are automatically determined.

The determining unit may be further configured to determine a growth state of the fertile ovum on the basis of the time-series change of the motion amount of the cell in the fertile ovum.

The determining unit may further configured to determine that a state of the fertile ovum, in which a total value of motion speed vectors of the cell in the fertile ovum is not less than a first threshold value and change of the motion speed vectors per unit time is approximately zero, is a lag-phase.

Therefore, the lag-phase (cell inactive phase) of the fertile ovum is automatically determined.

The determining unit may be further configured to determine that a state of the fertile ovum, in which a total value of motion speed vectors of the cell in the fertile ovum is more than a first threshold value and change of the motion speed vectors per unit time is not zero, is a degenerative cell proportion of less than 15%.

The determining unit may be further configured to determine that a state of the fertile ovum, in which a total value of motion speed vectors of the cell in the fertile ovum is not more than a first threshold value and change of the motion speed vectors per unit time is approximately zero, is a degenerative cell proportion of not less than 15%.

The determining unit may be further configured to determine that a state of the fertile ovum, in which a motion average speed of the cell in the fertile ovum is greater than a second threshold value, is a degenerative cell proportion of not less than 15% and less than 50%.

The determining unit may be further configured to determine that a state of the fertile ovum, in which a motion average speed of the cell in the fertile ovum is less than a second threshold value, is a degenerative cell proportion of not less than 50%.

The position in the image of the fertile ovum may be a pixel position

According to an embodiment of the present technique, there is provided an information processing method, including:

obtaining a plurality of images of a fertile ovum captured in time series; generating, for each image of the fertile ovum, a probability image, wherein each position in the probability image represents the probability that at least part of the fertile ovum is present at the corresponding position in the image of the fertile ovum; calculating time-series transformation of the fertile ovum from the probability images over the time series, and calculating a feature amount of the fertile ovum based on the transformation.

According to an embodiment of the present technique, there is provided a program, that causes an information processing apparatus to execute the steps of: obtaining a plurality of original images of a fertile ovum captured in time series; generating, for each image of the fertile ovum, a probability image, wherein each position in the probability image represents the probability that at least part of the fertile ovum is present at the corresponding position in the image of the fertile ovum; calculating time-series transformation of the fertile ovum from the probability images over the time series, and calculating a feature amount of the fertile ovum based on the transformation.

According to an embodiment of the present technique, there is provided an observation system, including: an image-capture unit configured to capture a plurality of images of a fertile ovum in time series; and an information processing apparatus including an image obtaining unit configured to obtain the plurality of images captured by the image-capture unit, a recognizing unit including a probability image generating unit configured to generate, for each image of the fertile ovum, a probability image, wherein each position in the probability image represents the probability that at least part of the fertile ovum is present at the corresponding position in the image of the fertile ovum; and a feature amount calculating unit configured to calculate time-series transformation of the fertile ovum from the probability images over the time series, and calculate a feature amount of the fertile ovum based on the transformation.

Advantageous Effects of Invention

As described above, according to the present technique, it is possible to provide an information processing apparatus, an information processing method, a program, and an observation system that helps evaluation of a fertile ovum under observation with a high degree of accuracy. These and other objects, features and advantages of the present disclosure will become more apparent in light of the following detailed description of best mode embodiments thereof, as illustrated in the accompanying drawings.

BRIEF DESCRIPTION OF DRAWINGS

FIG. 13 is a diagram schematically showing captured images of a fertile ovum in this embodiment.

FIG. 15 is a diagram schematically showing captured images of a fertile ovum in this embodiment.

DESCRIPTION OF EMBODIMENTS

Figure 1:
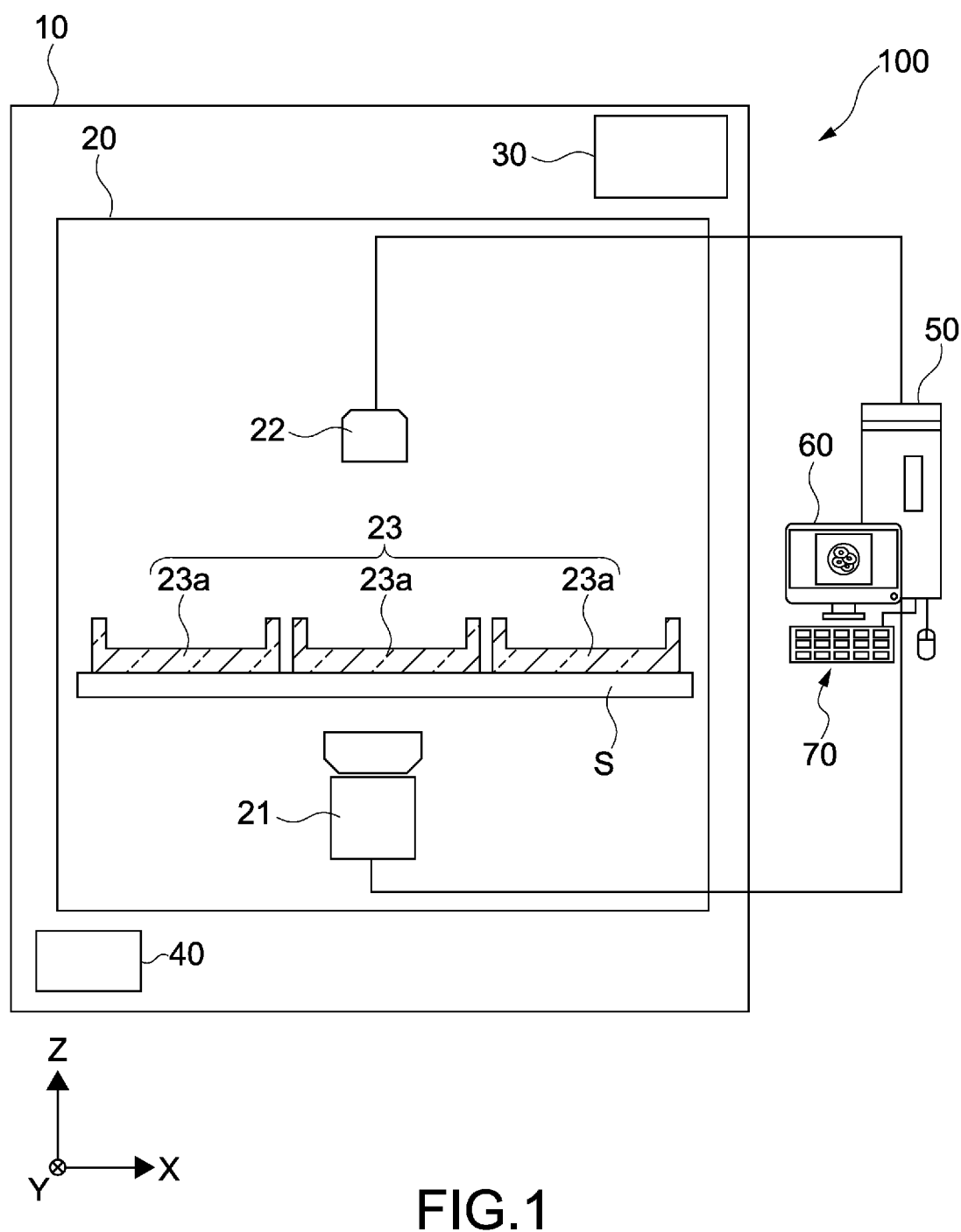
FIG. 1 is a diagram schematically showing a configuration example of the observation system according to a first embodiment of the present technique.

Hereinafter, embodiments of the present technique will be described with reference to the drawings. In the drawings, perpendicular X axis, Y axis, and Z axis are shown as necessary. The X axis, the Y axis, and the Z axis are common in all the drawings.

First Embodiment (Configuration of Observation System)

FIG. 1 is a diagram schematically showing a configuration example of an observation system 100 according to a first embodiment of the present technique. As shown in FIG. 1, the observation system 100 includes an incubator 10, an observation device 20, a humidity-temperature-gas controller unit 30, a detector unit 40, an information processing apparatus 100, a display device 60, and an input unit 70.

The incubator 10 is a culturing device, in which the observation device 20, the humidity-temperature-gas controller unit 30, and the detector unit 40 are housed, and has a function of keeping the temperature, the humidity, and the like of the inside of the culturing device constant. The incubator 10 allows arbitrary gas to flow into the incubator 10. The kind of the gas is not specifically limited and is, for example, nitrogen, oxygen, carbon dioxide, or the like.

The observation device 20 includes an image-capture unit 21, a light source 22, and a culture dish group 23. The image-capture unit 21 is configured to capture images of fertile ova F (see FIG. 3) held in the culture dish 23a (petri dish) in time series, and be capable of generating original images of the fertile ova F. This original image represents an image before being subjected to image processing by a recognizing unit 53 to be described later, and the fertile ova F appear in the image as they are. The same applies to the original image described below.

The image-capture unit 21 includes a lens barrel, a solid state image sensor, a drive circuit that drives them, and the like. The lens barrel includes a group of lenses capable of moving in a light-axis direction (Z-axis direction). The solid state image sensor captures light from an object passing through the lens barrel, and is a CMOS (Complementary Metal Oxide Semiconductor), a CCD (Charge Coupled Device), or the like.

The image-capture unit 21 is configured to be capable of moving in the light-axis direction (Z-axis direction) and the horizontal direction (direction perpendicular to Z-axis direction). The image-capture unit 21 captures images of the fertile ova F held in the culture dish 23a while moving in the horizontal direction. Further, the image-capture unit 21 may be configured to be capable of capturing not only still images but also motion images.

Typically, the image-capture unit 21 of the present embodiment is a visible camera. Not limited to this, the image-capture unit 21 may be an infrared (IR) camera, a polarization camera, or the like.

When the image-capture unit 21 captures images of the fertile ova F in the culture dish 23a, the light source 22 irradiates the culture dish 23a with light. The light source 22 is an LED (Light Emitting Diode) or the like that irradiates the culture dish 23a with light having a certain wavelength, for example. Where the light source 22 is an LED, for example, a red LED that irradiates the culture dish 23a with light having a wavelength of 640 nm is used.

The culture dish group 23 includes the plurality of culture dishes 23a. The culture dish group 23 is mounted on an observation stage S between the image-capture unit 21 and the light source 22. The observation stage S is transparent, and allows the light emitted from the light source 22 to pass therethrough.

Figure 2:
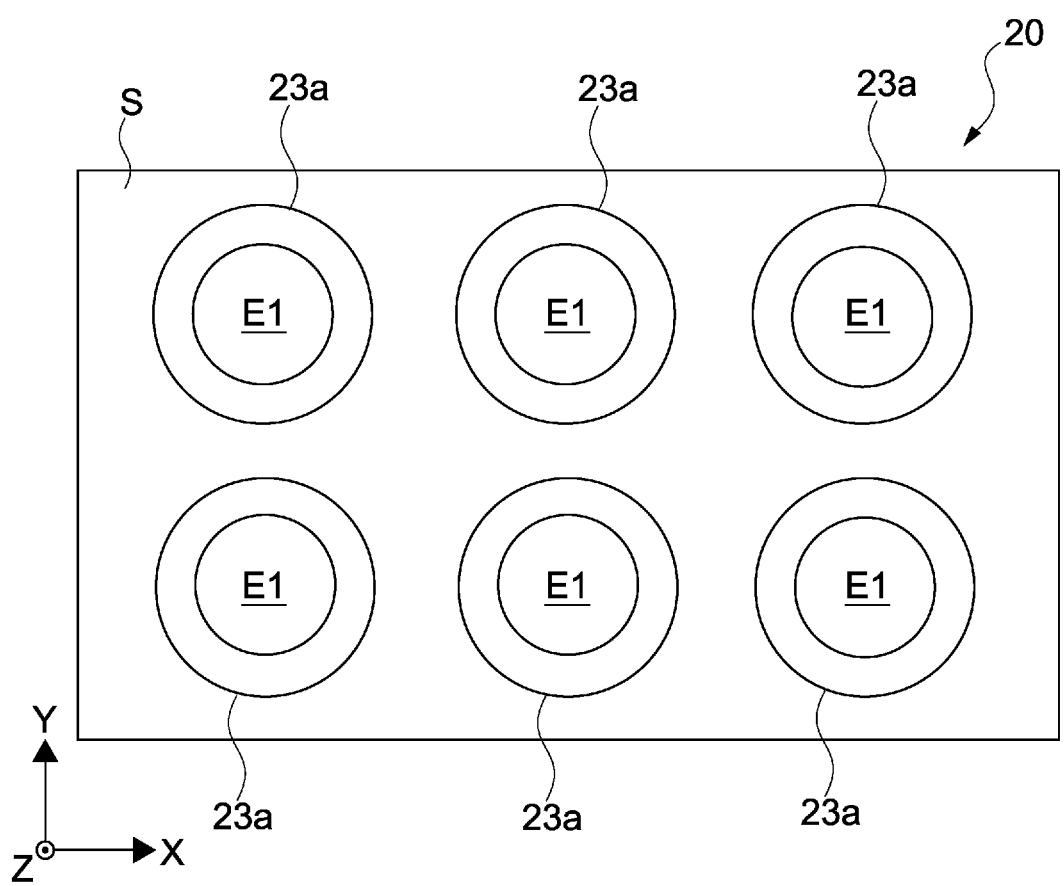
FIG. 2 is a diagram schematically showing the culture dish group mounted on the observation stage of the observation device seen from the light source side.

FIG. 2 is a diagram schematically showing the culture dish group 23 mounted on the observation stage S of the observation device 20 seen from the light source 22 side. As shown in FIG. 2, for example, the six culture dishes 23a are mounted on the observation stage S in a matrix, i.e., three in the X-axis direction and two in the Y-axis direction.

Figure 3:
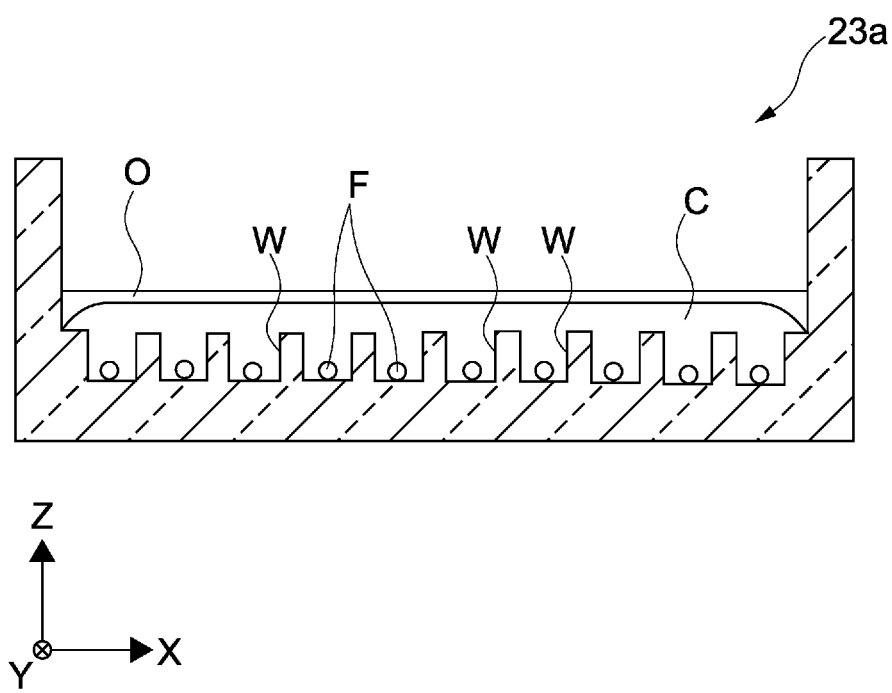
FIG. 3 is a diagram schematically showing a cross-section of the culture dish of this embodiment.

FIG. 3 is a diagram schematically showing a cross-section of the culture dish 23a. As shown in FIG. 3, the culture dish 23a has a plurality of wells W. The wells W of the culture dish 23a are arrayed in a matrix (see FIG. 5). Each well W is capable of holding one fertile ovum F.

A culture solution C and oil O are injected into the culture dish 23a having the wells W. The oil O coats the culture solution C to thereby have a function of preventing the culture solution C from evaporating.

Figure 4:
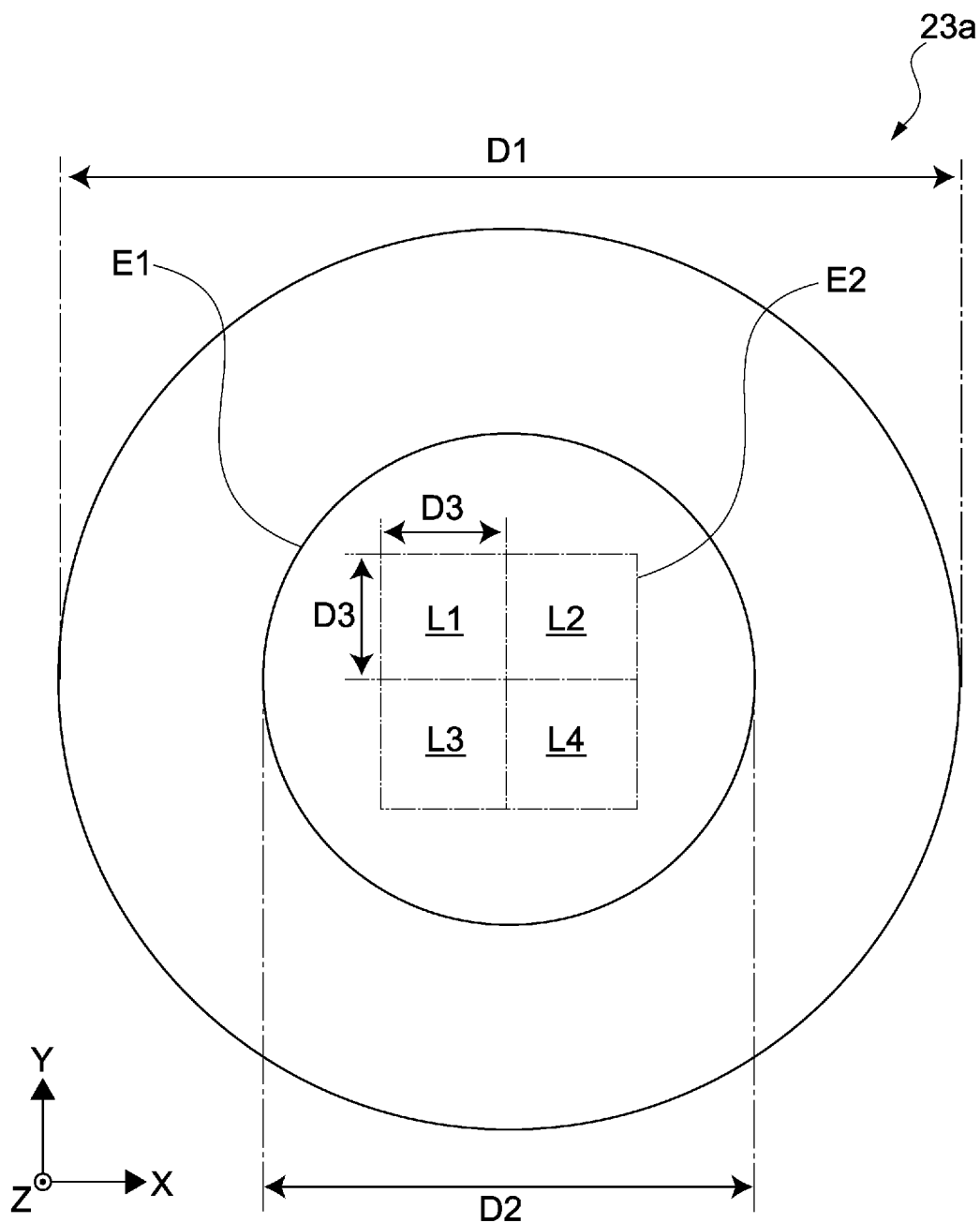
FIG. 4 is a diagram schematically showing the culture dish seen from the light source side.

FIG. 4 is a diagram (plan view) schematically showing the culture dish 23a seen from the light source 22 side. The culture dish 23a has a well area E1 in which the plurality of wells W are formed. A diameter D1 of the culture dish 23a and a diameter D2 of the well area E1 are not particularly limited. For example, the diameter D1 is about 35 mm, and the diameter D2 is about 20 mm.

The well area E1 has an image-capture region E2, the image-capture unit 21 taking images of the image-capture region E2. As shown in FIG. 2, the image-capture region E2 is equally divided into four image-capture areas L1 to L4. A length D3 of one side of each of the image-capture areas L1 to L4 is, for example, about 5 mm.

Figure 5:
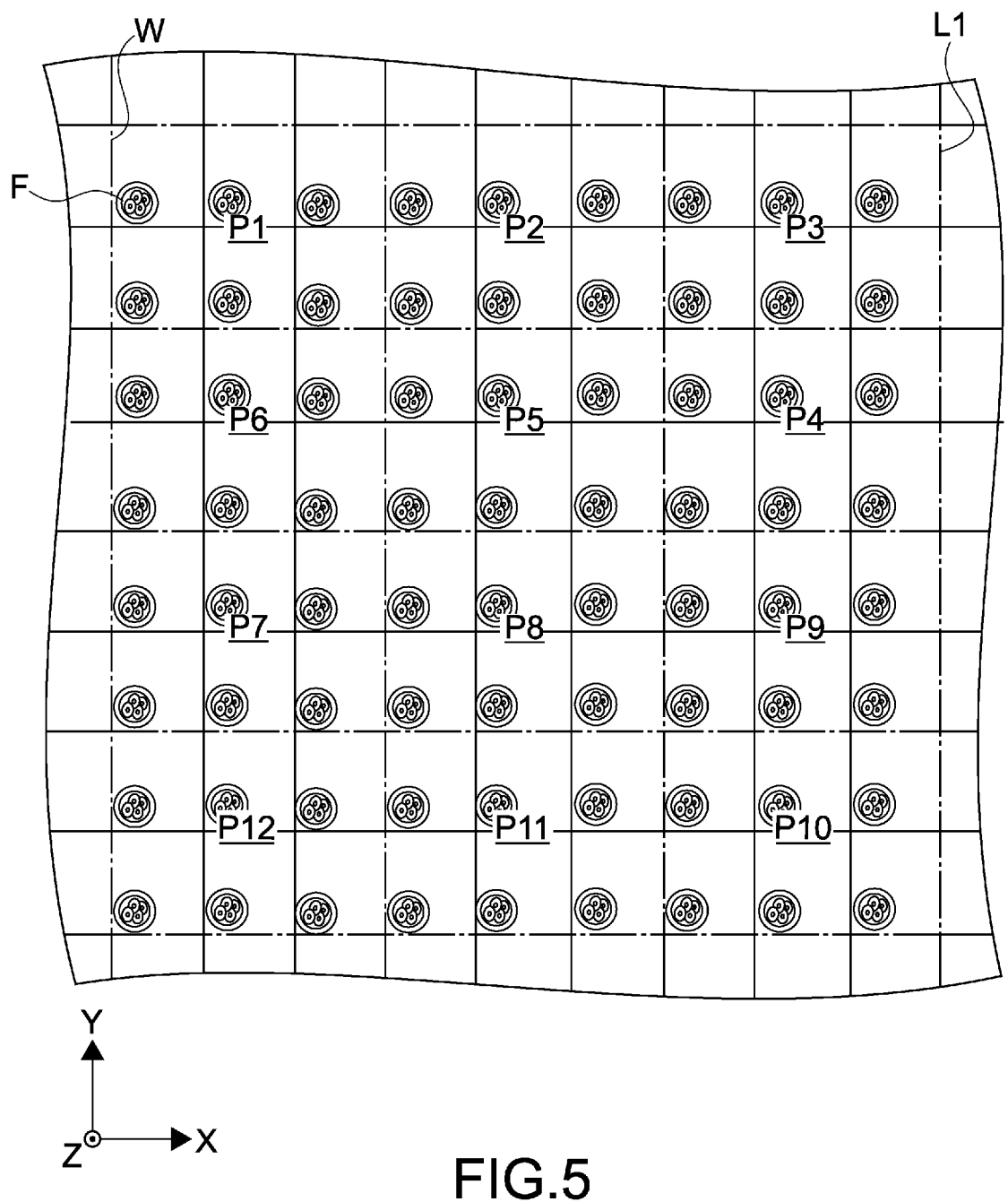
FIG. 5 is an enlarged diagram schematically showing the image-capture area of the culture dish seen from the light source side.

FIG. 5 is an enlarged diagram schematically showing the image-capture area L1 seen from the light source 22 side. The image-capture area L1 includes the 72 wells W out of the plurality of wells W in the well area E1, and is equally divided into twelve POS (position) areas.

Each of the POS areas P1 to P12 includes the six wells W, i.e., three wells W in the X-axis direction and two wells W in the Y-axis direction. According to the present embodiment, in the image obtaining step (described later) (see FIG. 7), the image-capture unit 21 captures images of the fertile ova F held in the wells W of each POS area in time series. Note that FIG. 5 is a diagram schematically showing the enlarged image-capture area L1. The structure of each of the image-capture areas L2 to L4 is similar to the structure of the image-capture area L1.

The material of the culture dish 23a is not particularly limited. The culture dish 23a is made from, for example, an inorganic material such as glass and silicon, or made from an organic material such as polystyrene resin, polyethylene resin, polypropylene resin, ABS resin, nylon, acrylic resin, fluororesin, polycarbonate resin, polyurethane resin, methylpentene resin, phenol resin, melamine resin, epoxy resin, vinyl chloride resin, and other organic materials. The culture dish 23a is a transparent material that allows the light emitted from the light source 22 to pass therethrough. Alternatively, a part of the culture dish 23a, through which no light emitted from the light source 22 passes, may be made from the above-mentioned materials or made from a metal material.

The humidity-temperature-gas controller unit 30 is configured to control the temperature and the humidity of the inside of the incubator 10 and gas introduced into the incubator 10 to thereby make the environment appropriate to growing of the fertile ovum F. The humidity-temperature-gas controller unit 30 is capable of controlling the temperature of the incubator 10 at about 38° C., for example.

The detector unit 40 is wirelessly connected to the information processing apparatus 100, and is configured to detect the temperature, the humidity, and the atmospheric pressure of the inside of the incubator 10, the illuminance of the light source 22, and the like, and output the detected results to the information processing apparatus 100. The detector unit 40 is, for example, a solar-panel-driven or battery-driven IoT (Internet of Things) sensor or the like, and may be of any kind.

The information processing apparatus 100 includes hardware necessary for a computer such as a CPU (Central Processing Unit), a ROM (Read Only Memory), a RAM (Random Access Memory), and an HDD (Hard Disk Drive). When the CPU loads a program of the present technique stored in the ROM or the HDD in the RAM and executes the program, the CPU controls operations of the respective blocks (described later) of the information processing apparatus 100.

For example, the program stored in any kind of a recording medium (internal memory) is installed in the information processing apparatus 100. Alternatively, the program may be installed via the Internet or another network. In the present embodiment, for example, the information processing apparatus 100 is a PC (Personal Computer) or the like, but the information processing apparatus 100 may be an arbitrary computer other than a PC.

The display device 60 is configured to be capable of displaying images and the like captured by the image-capture unit 21. The display device 60 is, for example, a liquid crystal display device, an organic EL (Electro-Luminescence) display device, or the like.

The input unit 70 includes operation devices such as a keyboard and a mouse in which operations are input by a user. In the present embodiment, the input unit 70 may be a touch panel or the like with the display device 60.

Figure 6:
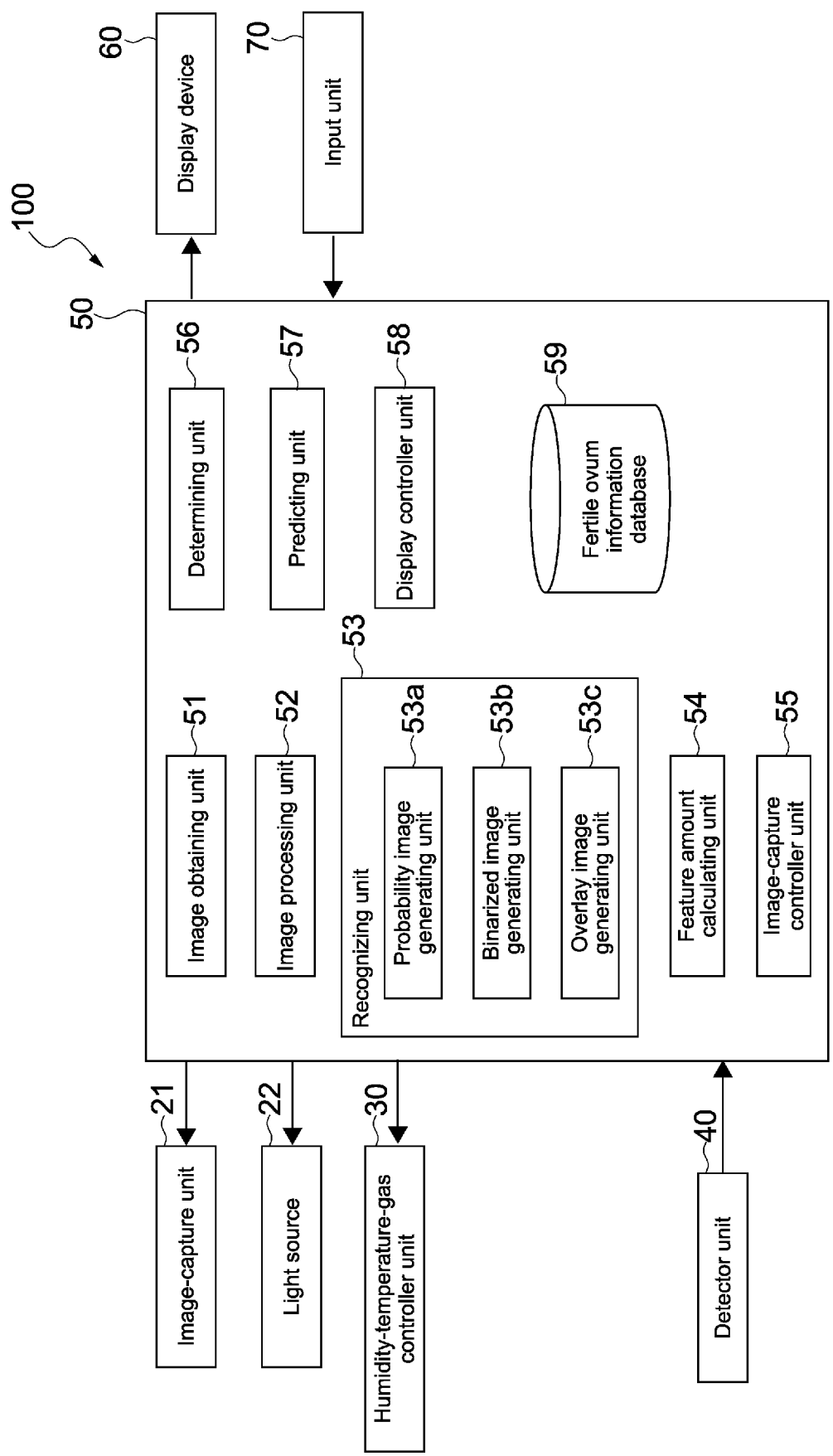
FIG. 6 is a function block diagram showing a configuration example of the observation system.

Next, a configuration of the information processing apparatus 100 will be described. FIG. 6 is a function block diagram showing a configuration example of the observation system 100.

(Information Processing Apparatus)

As shown in FIG. 6, the information processing apparatus 100 includes an image obtaining unit 51, an image processing unit 52, the recognizing unit 53, a feature amount calculating unit 54, an image-capture controller unit 55, a determining unit 56, a predicting unit 57, a display controller unit 58, and a fertile ovum information database 59.

The image obtaining unit 51 is configured to obtain a plurality of original images of the fertile ova F captured in time series by the image-capture unit 21, and output the obtained original images to the image processing unit 52, the display controller unit 58, and the fertile ovum information database 59.

The image processing unit 52 is configured to process (trim) the original images obtained from the image obtaining unit 51, and output the processed original images to a probability image generating unit 53*a*, an overlay image generating unit 53*c* (which will be described later), the display controller unit 58, and the fertile ovum information database 59.

The recognizing unit 53 includes the probability image generating unit 53*a*, a binarized image generating unit 53*b*, and the overlay image generating unit 53*c*. The probability image generating unit 53*a* is configured to generate probability images from the original images obtained from the image processing unit 52, and output the probability images to the binarized image generating unit 53*b*, the feature amount calculating unit 54, the display controller unit 58, and the fertile ovum information database 59. Each of the probability images represents probability that the fertile ova F is present.

The binarized image generating unit 53*b* is configured to generate binarized images from the probability images obtained from the probability image generating unit 53*a* by processing the probability images by means of a binarizing process with a predetermined threshold value. The binarized image generating unit 53*b* is further configured to output the binarized images to the overlay image generating unit 53*c*, the feature amount calculating unit 54, the display controller unit 58, and the fertile ovum information database 59.

The overlay image generating unit 53*c* is configured to generate overlay images by overlaying the original images obtained from the image processing unit 52 and the binarized images obtained from the binarized image generating unit 53*b*. The overlay image generating unit 53*c* is further configured to output the overlay images to the feature amount calculating unit 54, the display controller unit 58, and the fertile ovum information database 59.

According to the present embodiment, the recognizing unit 53 is configured to be capable of recognizing the fertile ovum F on the basis of at least one of the probability images, the binarized images, and the overlay images.

The feature amount calculating unit 54 is configured to calculate time-series transformation of the fertile ovum F from at least one of the probability images, the binarized images, and the overlay images obtained from the probability image generating unit 53*a*, the binarized image generating unit 53*b*, and the overlay image generating unit 53*c*, respectively. The feature amount calculating unit 54 is further configured to be capable of calculating a feature amount of the fertile ovum F on the basis of the transformation.

The feature amount calculating unit 54 is further configured to output numerical data about the calculated transformation and the calculated feature amount to the image-capture controller unit 55, the determining unit 56, the predicting unit 57, the display controller unit 58, and the fertile ovum information database 59.

The image-capture controller unit 55 is configured to be capable of controlling the image-capture unit 21 and the light source 22 on the basis of output from the feature amount calculating unit 54, time of capturing the images of the fertile ova F being changed under the control.

For example, the image-capture controller unit 55 controls the image-capture unit 21 and the light source 22 on the basis of the transformation or feature amount output from the feature amount calculating unit 54, the image-capture intervals of capturing images of the fertile ova F being shortened under the control. Under the control, it is possible to irradiate the fertile ova F with light only at the time of obtaining data, which is very important to evaluate the quality of each of the fertile ova F. Therefore, the total time period, in which the fertile ova F under observation are irradiated with light from the light source 22, is shortened, and photo-damages (phototoxicity) to the fertile ova F are reduced.

The photo-damages (phototoxicity) include photo-damages, thermal damages, and other damages to DNA and chromosomes affected by light. The image-capture controller unit 55 may control the image-capture unit 21 and the light source 22 on the basis of not only the transformation or feature amount output from the feature amount calculating unit 54 but also time of capturing the fertile ova F, the growth stages, and the like.

Further, the image-capture controller unit 55 is configured to be also capable of controlling the light source 22 and the humidity-temperature-gas controller unit 30 on the basis of output from the detector unit 40. As a result, the temperature and the humidity of the inside of the incubator 10 and the illuminance of the light source 22 are adjusted.

The determining unit 56 determines quality of each of the fertile ova F on the basis of the feature amount output from the feature amount calculating unit 54. Further, the determining unit 56 determines also the growth state of each of the fertile ova F on the basis of the transformation output from the feature amount calculating unit 54.

The determining unit 56 outputs the determination results obtained on the basis of the feature amount and the transformation to the display controller unit 58 and the fertile ovum information database 59.

The predicting unit 57 is configured to calculate at least one of an incubation rate, an implantation rate, a pregnancy rate, a conception rate, a miscarriage rate, a birthweight, a birth rate, a breeding value of a grown-up, and the like of each of the fertile ova F on the basis of at least one of the transformation and the feature amount output from the feature amount calculating unit 54. The predicting unit 57 is further configured to output the predictive values to the display controller unit 58 and the fertile ovum information database 59.

The display controller unit 58 is configured to display, on the display device 60, the original images output from the image obtaining unit 51 and the image processing unit 52, the probability images output from the probability image generating unit 53*a*, the binarized images output from the binarized image generating unit 53*b*, the overlay images output from the overlay image generating unit 53*c*, the transformation and the feature amount output from the feature amount calculating unit 54, the determination results of the fertile ova F output from the determining unit 56, the predictive values output from the predicting unit 57, various images and quality information retrieved from the fertile ovum information database 59, and the like.

The fertile ovum information database 59 is configured to store the original images output from the image obtaining unit 51 and the image processing unit 52, the probability images output from the probability image generating unit 53*a*, the binarized images output from the binarized image generating unit 53b, and the overlay images output from the overlay image generating unit 53c.

The fertile ovum information database 59 is further configured to store the transformation and the feature amount output from the feature amount calculating unit 54, the determination results of the fertile ova F output from the determining unit 56, the predictive values output from the predicting unit 57, input information input from the input unit 70, and the like.

(Quality Evaluation)

Figure 7:
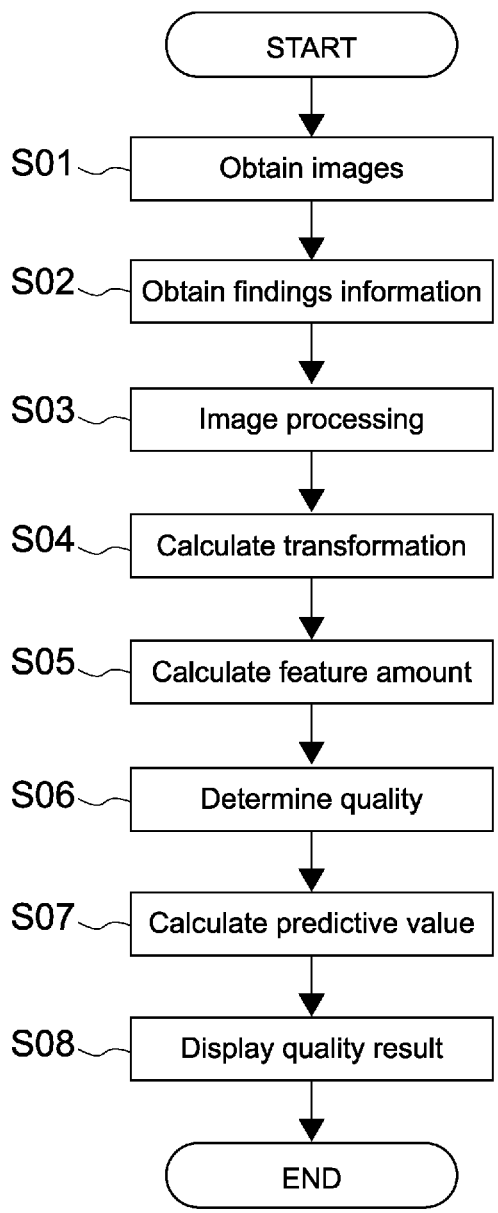
FIG. 7 is a flowchart showing a method of evaluating quality of each of the fertile ova by the information processing apparatus of this embodiment.

FIG. 7 is a flowchart showing a method of evaluating quality of each of the fertile ova F by the information processing apparatus 100. With reference to FIG. 7 as necessary, a method of evaluating quality of each of the fertile ova F will be described hereinafter. Note that as will be described later, a method of evaluating quality of each of the fertile ova F where a zona pellucida of each of the fertile ova F and a cell in each of the fertile ova F are recognized will be described in the present embodiment.

(Step S01: Obtain Images)

Figure 8:
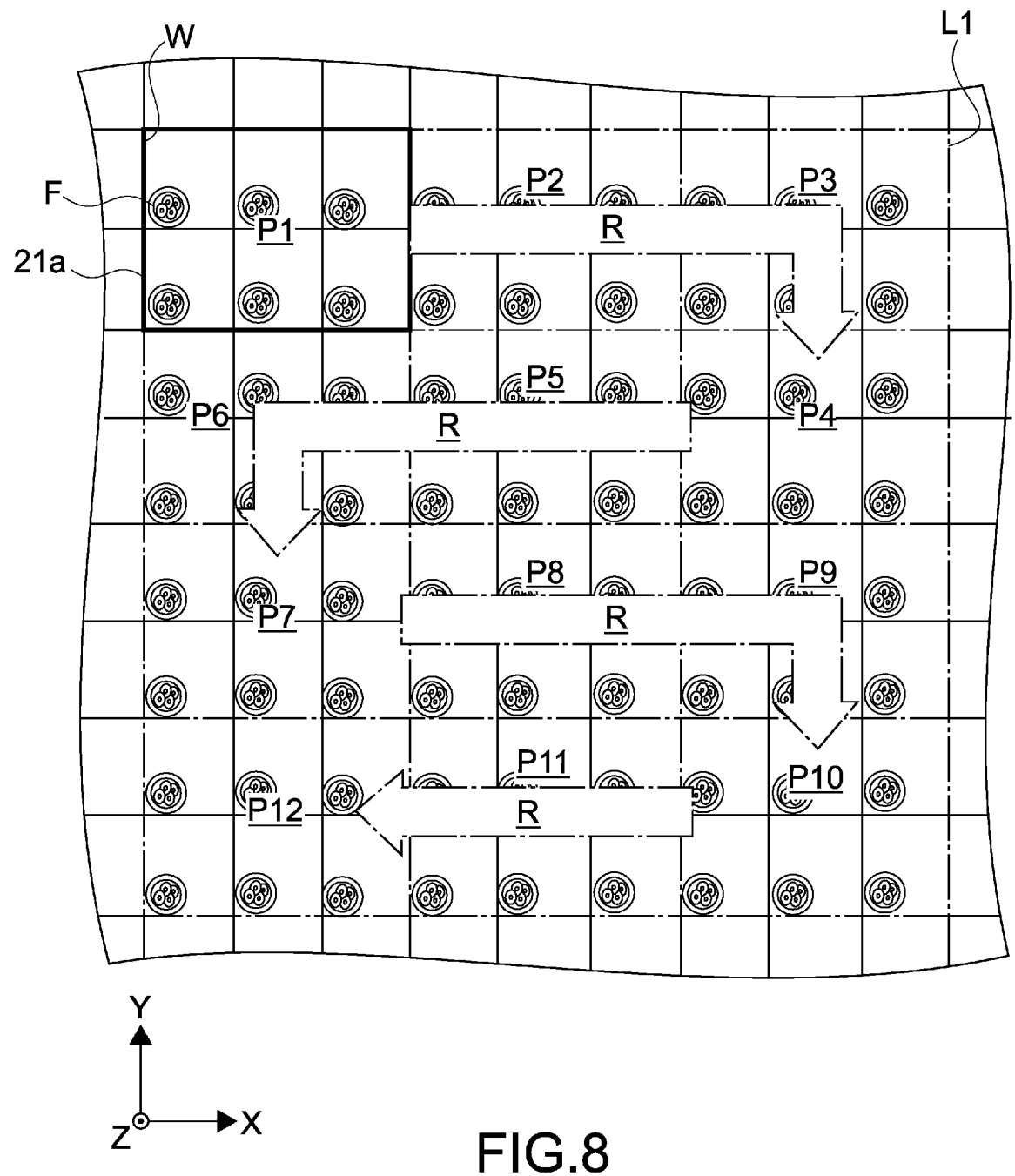
FIG. 8 is a diagram schematically showing how the image-capture unit of the observation system captures images of the plurality of fertile ova.

FIG. 8 is a diagram schematically showing how the image-capture unit 21 captures images of the plurality of fertile ova F, and showing a route of the image-capture unit 21 moving.

Firstly, the image-capture unit 21 captures images of the plurality of fertile ova F held in the plurality of wells W one-to-one for each POS (Position) area in time series. As shown in FIG. 8, at this time, a field-of-view range 21a of the image-capture unit 21 moves in the order from the POS area P1 to the POS area P12 at intervals of about 3 seconds along a moving route R.

Then this process is executed for all the culture dishes 23a mounted on the observation stage S, which is repeated a predetermined times. As a result, a plurality of original images, each including six fertile ova F, are generated. The plurality of original images are transferred to the image obtaining unit 51 (the information processing apparatus 100).

Figure 9:
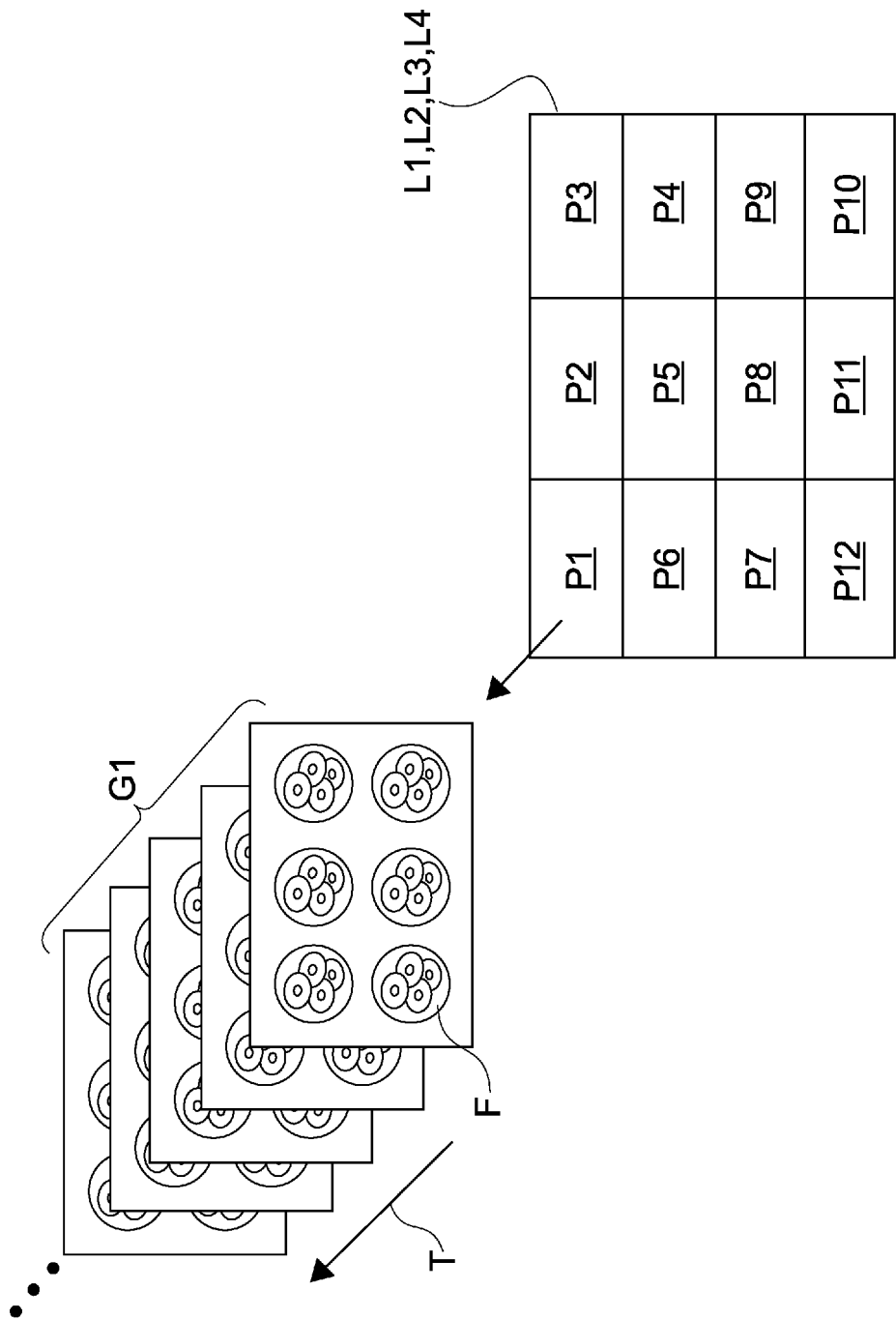
FIG. 9 is a diagram conceptionally showing a plurality of original images of the present technique.

FIG. 9 is a diagram conceptually showing the plurality of original images. As shown in FIG. 9, in the present embodiment, the plurality of original image are generated in time series along a time axis T for each of the POS areas P1 to P12. In the present description, the image group shown in FIG. 9 will be referred to as a plurality of first time-series images G1.

The image-capture intervals and the number of capture of the image-capture unit 21 of the observation system 100 may be arbitrarily configured. For example, the image-capture time period is 1 week, the image-capture interval is 15 minutes, and 9 stacks of images are captured where the focal length is changed in the depth direction (Z-axis direction). In this case, about 6000 stacked images each including six fertile ova F are obtained for each one of the POS areas. As a result, three-dimensional images of the fertile ova F may be obtained.

The image obtaining unit 51 outputs the plurality of first time-series images G1, which are transferred from the image-capture unit 21, to the image processing unit 52, the display controller unit 58, and the fertile ovum information database 59. The fertile ovum information database 59 stores the plurality of first time-series images G1.

(Step S02: Obtain Findings Information)

The display controller unit 58 retrieves the plurality of first time-series images G1 stored in the fertile ovum information database 59, and outputs the plurality of first time-series images G1 to the display device 60. Then, the display device 60 displays the plurality of first time-series images G1.

Subsequently, a specialist such as an embryologist evaluates the quality (growth state, number of cells, cell symmetric property, number of pronuclei, number of polar bodies, number of nuclei in a blastomere, fragment, etc.) of each fertile ovum F on the basis of his/her morphological findings with reference to the plurality of first time-series images G1 displayed on the display device 60. The evaluation result of the fertile ovum F, which is evaluated by the embryologist, is input in the input unit 70 and output to the fertile ovum information database 59. The evaluation result of the fertile ovum F is stored in the fertile ovum information database 59 and treated as first quality data about the fertile ovum F.

Note that, in the present embodiment, a method of evaluating quality of the fertile ovum F by an embryologist is not particularly limited. For example, in Step S02, typically, an embryologist evaluates qualities of all the six fertile ova F in the plurality of first time-series images G1 for each of the POS areas P1 to P12. Not limited to this, an embryologist may evaluate qualities of some of the fertile ova F. Further, an embryologist may refer to all or some of the stacked images of the 9 stacks of each fertile ovum F to evaluate the fertile ovum F.

(Step S03: Image Processing)

Figure 10:
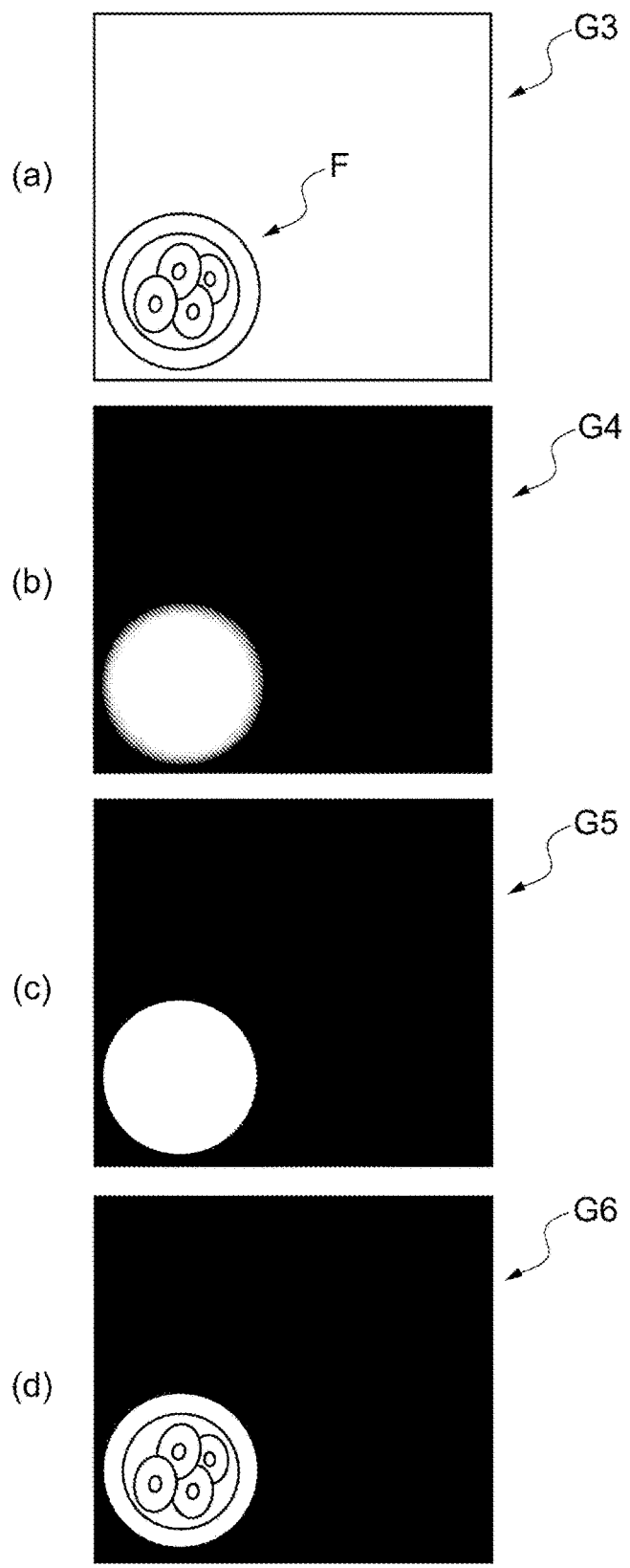
FIG. 10 is a diagram schematically showing various images indicating a process of image processing by a recognizing unit of the present technique.

FIG. 10 is a diagram schematically showing various images indicating a process of image processing by the recognizing unit 53 of the present embodiment. The image processing unit 52 processes (trims) the plurality of first time-series images G1 obtained from the image obtaining unit 51 for a unit of the fertile ovum F. As a result, the image processing unit 52 generates a plurality of original images G3 each including one fertile ovum F (see FIG. 10(a), FIG. 11). Subsequently, the image processing unit 52 outputs the plurality of original images G3 to the probability image generating unit 53a, the overlay image generating unit 53c, the display controller unit 58, and the fertile ovum information database 59. The fertile ovum information database 59 stores the plurality of original images G3. By trimming the first time-series images to produce original images, the amount of memory required to store the original images is reduced. It should be noted that although the above describes trimming the plurality of first time-series images G1, the disclosure is not limited to this and this trimming step is optional.

Figure 11:
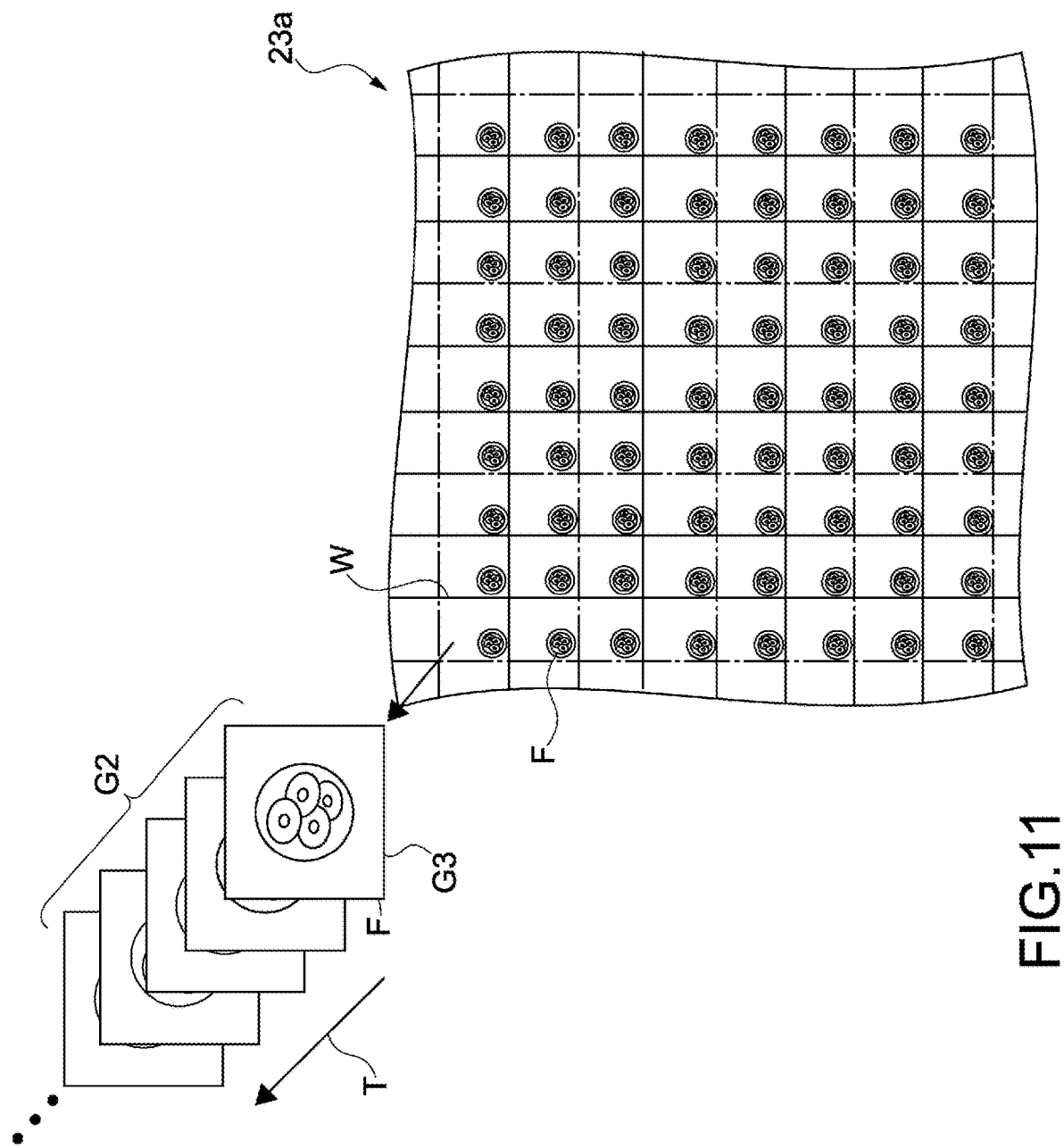
FIG. 11 is a diagram conceptionally showing the plurality of original images of the present technique.

FIG. 11 is a diagram conceptually showing the plurality of original images G3. As shown in FIG. 11, the plurality of original images G3 each including one fertile ovum F are generated in time series along the time axis T for each of the plurality of wells W. In the present description, the image group shown in FIG. 11 will be referred to as a plurality of second time-series images G2.

The probability image generating unit 53a analyzes the plurality of second time-series images G2 output from the image processing unit 52 in a predetermined way, and thereby generates probability images G4 (see FIG. 10(b)) corresponding to the plurality of original images G3. The probability image generating unit 53a outputs the probability images G4 to the binarized image generating unit 53b and the fertile ovum information database 59.

Specifically, the probability image generating unit 53a generates the probability images G4 for the respective plurality of original images G3, in which probability that a, in this example, zona pellucida is present in the fertile ova F is calculated for each pixel, by means of a deep learning analysis using an image, in which a zona pellucida of a fertile ovum has been recognized, stored in the fertile ovum information database 59 in advance, as teaching data. In other words, for each pixel position, the probability that a part of a zona pellucida is provided at that pixel position is determined. This means that the probability image is a probability map showing the probability of the presence of a specific part of the fertile ovum at a position in the image. This image may be the original image or may be the untrimmed image. Of course, although the above describes determining the probability of the presence of a zona pellucida at a pixel position, the disclosure is not so limited. For example, the probability of the presence of a zona pellucida (or other feature of the ferile ovum) at a position of a block of pixels may be determined using a block matching technique.

At this time, as the teaching data, for example, a large amount of captured images of a fertile ovum similar to the fertile ovum F of the present embodiment, in which a zona pellucida of the fertile ovum has been recognized by performing a labelling process by visual observation, are used.

The probability images G4 output to the fertile ovum information database 59 are stored in the fertile ovum information database 59 as new teaching data used when generating probability images from the original images G3, and the fertile ovum information database 59 is updated.

Subsequently, the binarized image generating unit 53b generates binarized images G5 (see FIG. 10(c)) corresponding to the plurality of probability images G4 by processing the plurality of probability images G4 output from the probability image generating unit 53a by means of a binarizing process with a predetermined threshold value for each pixel. The binarized image generating unit 53b outputs the binarized images G5 to the overlay image generating unit 53c.

Specifically, the binarized image generating unit 53b generates the binarized images G5 by processing the plurality of probability images G4 by means of, for example, a binarizing process of setting a pixel, in which probability that a zona pellucida is present is less than a threshold probability of, for example, 50%, to 0 (black) and setting a pixel, in which probability that a zona pellucida is present is not less than 50%, to 1 (white) for each pixel. As a result, for example, the profile line of the zona pellucida in the probability images G4 is extracted. In other words, the binarized image generating unit 53b compares the probability of the presence of a part of a zona pellucida with a threshold probability and, where the value of the probability of the presence is below the threshold, the pixel value is set to black and where the value of the probability of the presence is above the threshold, the pixel value is set to white. It should be noted that by making the threshold probability 50%, the accuracy of the recognition of the fertile ovum can be stabilized. This is especially when combined with image processing where the brightness is normalized as it is possible to process an image with an intermediate value (50%) of white and black, of course, however, although the threshold probability is noted as being 50%, any appropriate threshold probability, such as 45%, 30% or the like may be selected.

Subsequently, the overlay image generating unit 53c generates overlay images G6 (see FIG. 10(d)), in which, for example, a zona pellucida has been recognized with probability of not less than threshold probability of, for example, 50%, for the plurality of original images G3 by overlaying the plurality of original images G3 (the plurality of second time-series images G2) output from the image processing unit 52 and the plurality of binarized images G5 output from the binarized image generating unit 53b. The overlay image generating unit 53c outputs the overlay images G6 to the feature amount calculating unit 54 and the fertile ovum information database 59.

Subsequently, the overlay image generating unit 53c forms a mask area along the part of recognized zona pellucida for each of the plurality of overlay images G6. As a result, only a part having probability that a zona pellucida is present, which is not less than 50%, for example, is masked.

The recognizing unit 53 of the present embodiment is capable of recognizing not only a zona pellucida of the fertile ova F but also cells (blastocyst, blastomere, morula, etc.) in the fertile ova F, pronucleus, polar body, nucleus in a blastomere, fragmentation, a translucent zone in a peripheral ooplasm, and the like by the image processing method described above. In embodiments to be described later, a method of evaluating quality where such cells are recognized will be described.

Note that typically, the recognizing unit 53 recognizes, but not limited to, a zona pellucida of the fertile ova F, a cell-blastocyst, a blastomere, a pronucleus, a polar body, a nucleus in a blastomere, fragmentation, Halo, and the like on the basis of the overlay images G6. In the present embodiment, the various parts of the fertile ova F described above may be recognized on the basis of the probability images G4 or the binarized images G5. Also the transformation, the feature amount, and time-series change of the motion amount of the cells in the fertile ova F to be described in the following embodiments may be calculated on the basis of the probability images G4 or the binarized images G5. This also applies to all the embodiments of the disclosure.

(Step S04: Calculate Transformation)

The feature amount calculating unit 54 analyzes the plurality of overlay images G6 output from the recognizing unit 53 in a predetermined way, and thereby calculates transformation of the fertile ovum F along the time axis T. The feature amount calculating unit 54 outputs numerical data about the transformation to the image-capture controller unit 55, the determining unit 56, the predicting unit 57, the display controller unit 58, and the fertile ovum information database 59. The fertile ovum information database 59 stores the numerical data output from the feature amount calculating unit 54 as reference data in the fertile ovum information database 59.

The numerical data about the transformation output to the fertile ovum information database 59 is stored in the fertile ovum information database 59 in association with first quality data (growth state, number of cells, cell symmetric property, fragment, etc.) about the fertile ovum F having the transformation evaluated in the above-mentioned Step S02, and treated as second quality data.

For example, the feature amount calculating unit 54 calculates inter-frame differential values of the plurality of overlay images G6 output from the recognizing unit 53, and calculates the transformation on the basis of the differential value. In other words, the difference in the fertile ovum between frames is used by the calculating unit 54 to calculate the transformation as the difference in a physiological characteristic of the fertile ovum over a period of time.

Alternatively, the feature amount calculating unit 54 may calculate a differential value between the mask area of one overlay images G6 and the mask area of another overlay images G6 of the plurality of mask areas formed on the plurality of overlay images G6 in the above-mentioned Step S03. In other words, the feature amount calculating unit 54 may calculate inter-frame differential values of only the mask areas, and calculate the transformation on the basis of the differential value.

As a result, occurrence of noises and mis-detection, which results from an interframe differential value calculated on the basis of the whole captured image of the fertile ovum F, is reduced. The transformation and a feature amount (described later) of the fertile ovum F may be calculated accurately.

The feature amount calculating unit 54 calculates, as the transformation, at least one of change of a diameter, an area, and thickness of a zona pellucida of the fertile ovum F. Further, change of an area of a blastocyst or a blastomere as the cell in the fertile ovum F is calculated. In other words, the change in a physiological characteristic of the fertile ovum is calculated as the transformation. As a result, since they are visualized as shown in the graph or the like, it is possible to objectively and quantitatively know the time-series contraction/dilation activity of a zona pellucida of the fertile ovum F and the cell in the fertile ovum F (see FIG. 16).

(Step S05: Calculate Feature Amount)

Subsequently, the feature amount calculating unit 54 analyzes the calculated transformation by means of a predetermined process, and thereby calculates a feature amount of the fertile ovum F. The feature amount calculating unit 54 outputs numerical data about the feature amount to the image-capture controller unit 55, the determining unit 56, the predicting unit 57, the display controller unit 58, and the fertile ovum information database 59. In other words, the feature amount is a numeric representation of the change of the physiological characteristic of the fertile ovum.

The numerical data about the feature amount, which is output to the fertile ovum information database 59, is stored in the fertile ovum information database 59 in association with the second quality data (quality data in which numerical data about the transformation and the first quality data are in association with each other) stored in the fertile ovum information database 59 in advance, and treated as fourth quality data.

Figure 12:
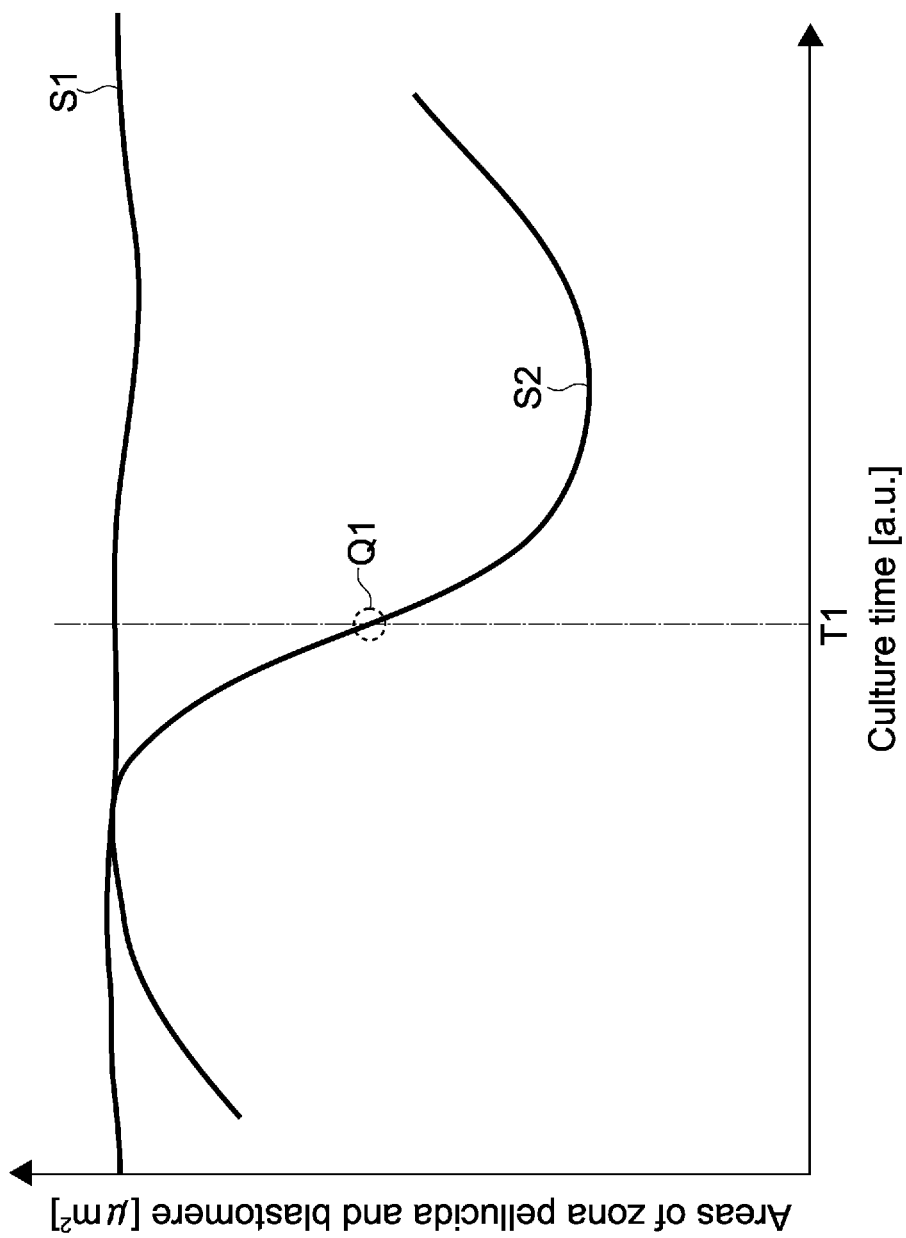
FIG. 12 is a diagram schematically showing the graph, which visualizes time-series transformation of the fertile ovum of this embodiment.

FIG. 12 is a graph showing time-series change of an area of the fertile ovum F with reference to the culture time. The S1 shown in FIG. 12 represents a graph showing change of an area of a zona pellucida, and the S2 shown in FIG. 12 represents a graph showing change of an area of a blastomere. Further, FIG. 13 is a diagram schematically showing captured images of the fertile ovum F. (a) of FIG. 13 is a diagram schematically showing a captured image of a sixteen-cell stage fertile ovum F. (b) of FIG. 13 is a diagram schematically showing a captured image of a morula stage fertile ovum F.

The feature amount calculating unit 54 calculates, as the feature amount, at least one of compaction time (when the physiological characteristic is where divided cells bind firmly together to form a single mass) and cleavage time of the fertile ovum F. As a result, as shown in FIG. 13, it is possible to quantitatively and objectively know the compaction time, the cleavage time, and the like when the growth stage of the fertile ovum F is changed from a sixteen-cell stage to a morula stage, for example.

In the example shown in FIG. 12, a culture time T1 corresponding to an inflection point Q1 of the graph S2 corresponds to the compaction time of the fertile ovum F. However, which point is set as the compaction time or the cleavage time may be arbitrarily determined on the basis of the graphs S1 and S2.

Figure 14:
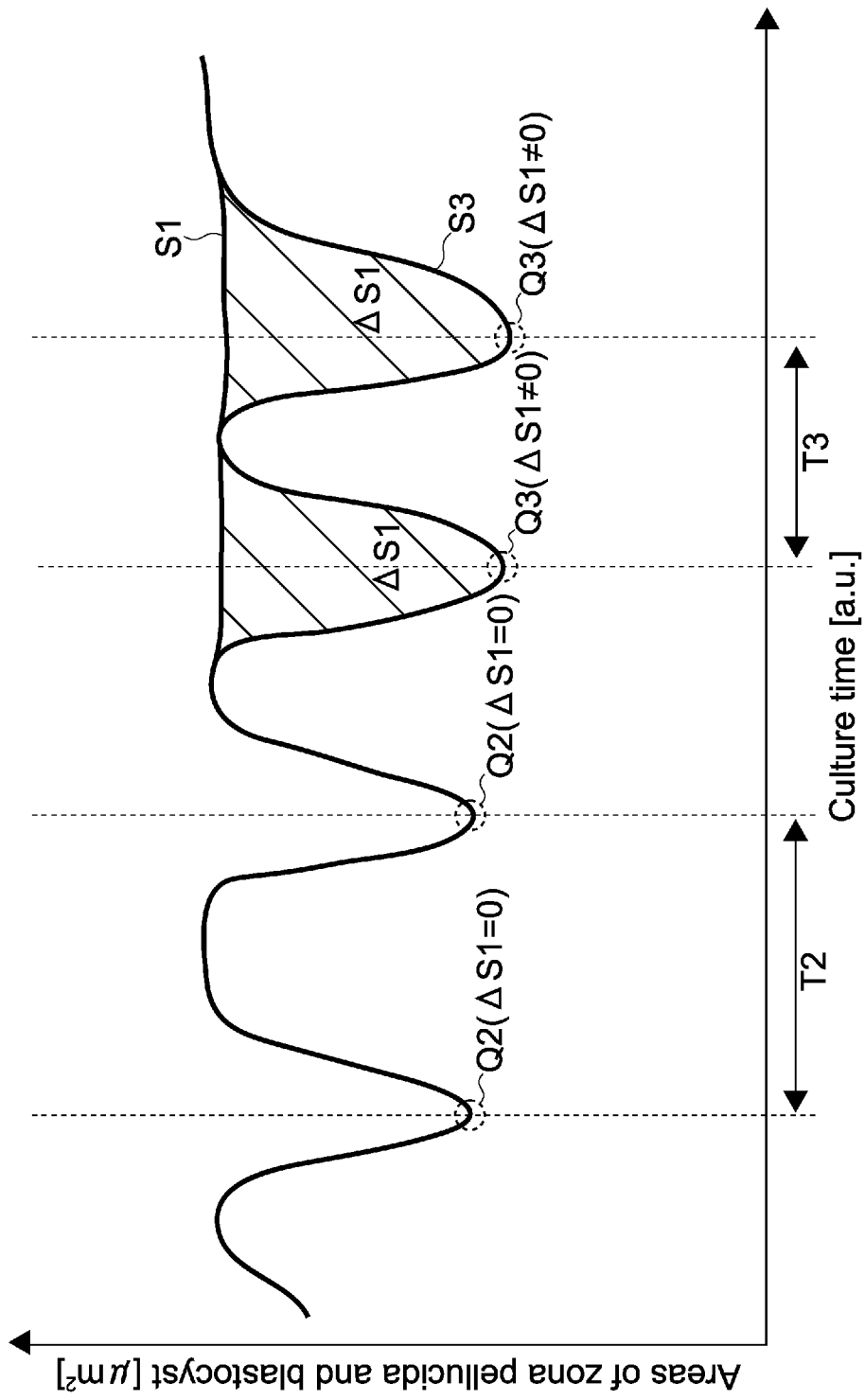
FIG. 14 is a diagram schematically showing the graph, which visualizes time-series transformation of the fertile ovum of this embodiment.

FIG. 14 is a graph showing time-series change of an area of the fertile ovum F with reference to the culture time. The S1 shown in FIG. 14 represents a graph showing change of an area of a zona pellucida, and the S3 shown in FIG. 14 represents a graph showing change of an area of a blastocyst. Further, FIG. 15 is a diagram schematically showing captured images of the fertile ovum F. (a) of FIG. 15 is a diagram schematically showing a captured image of a blastocyst-stage fertile ovum F, and (b) of FIG. 15 is a diagram schematically showing a state of the fertile ovum F, in which a blastocyst and a zona pellucida contract. (c) of FIG. 15 is a diagram schematically showing a state of the fertile ovum F, in which only a blastocyst contracts.

In the present embodiment, the feature amount calculating unit 54 is configured to calculate, as the feature amount, the number of times of contraction, a contraction diameter, a contraction speed, a contraction time period, contraction intervals, contraction strength, contraction frequency, the number of times of dilation, a dilation diameter, a dilation speed, a dilation time period, dilation intervals, dilation strength, and dilation frequency of a zona pellucida and a blastocyst on the basis of time-series change of a difference between an area of the zona pellucida and the blastocyst.

As a result, it is possible to quantitatively and objectively know the minute contraction/dilation activity of each of the zona pellucida and the blastocyst. In the example shown in FIG. 14, the number of times that a difference ΔS1 between an area S1 of the zona pellucida and an area S3 of the blastocyst is 0 in the culture time of the fertile ovum F is counted, and the number of times that the difference ΔS1 between the area S1 of the zona pellucida and the area S3 of the blastocyst is not 0 in the culture time of the fertile ovum F is counted. As a result, the number of times of contraction of the zona pellucida and the number of times of contraction of the blastocyst are obtained.

Specifically, the case where the difference ΔS1 is 0 at a peak Q2 of the graph S1 representing time-series change of the area of the zona pellucida is determined as the contraction activity (see (b) of FIG. 15) of the zona pellucida and the blastocyst, and the case where the difference ΔS1 is not 0 at a peak Q3 of the graph S3 representing time-series change of the area of the blastocyst is determined as the contraction activity (see (c) of FIG. 15) of the blastocyst.

Therefore, in FIG. 14, the number of peaks Q2 of the graph S1 where the difference ΔS1 is 0 corresponds to the number of times of contraction of the zona pellucida, and the number of peaks Q3 of the graph S3 where the difference ΔS1 is not 0 corresponds to the number of times of contraction of the blastocyst. Further, an interval T2 between the peaks Q2 corresponds to the contraction cycle of the zona pellucida and the blastocyst, and an interval T3 between the peaks Q3 corresponds to the contraction cycle of the blastocyst.

(Step S06: Determine Quality)

The determining unit 56 checks the numerical data about the transformation or the feature amount output from the feature amount calculating unit 54 against the fourth quality data corresponding to the transformation or the feature amount prestored in the fertile ovum information database 59. As a result, the determining unit 56 determines the quality, the growth state, and the like of the fertile ovum F.

At this time, the determining unit 56 selects, as the fourth quality data corresponding to the numerical data about the transformation or the feature amount, the fourth quality data including the numerical data most similar to the numerical data about the transformation or the feature amount. The determining unit 56 retrieves the selected fourth quality data from the fertile ovum information database 59.

Therefore, the determining unit 56 may automatically determine the quality, the growth state, and the like of the fertile ovum F on the basis of the transformation or the feature amount output from the feature amount calculating unit 54 by using the quality result obtained on the basis of morphological findings of the embryologist.

Next, the determining unit 56 outputs the determination result of the fertile ovum F, which is determined by checking the numerical data about the transformation or the feature amount against the fourth quality data, to the display controller unit 58 and the fertile ovum information database 59. As a result, the determination result is stored as new reference data (fourth quality data) in the fertile ovum information database 59, and the fertile ovum information database 59 is updated.

Where the feature amount calculating unit 54 calculates change of the diameter, the area, or the thickness of the zona pellucida of the fertile ovum F as the transformation in the above-mentioned Step S04, the determining unit 56 determines the growth state of the fertile ovum F on the basis of at least one of them.

Figure 16:
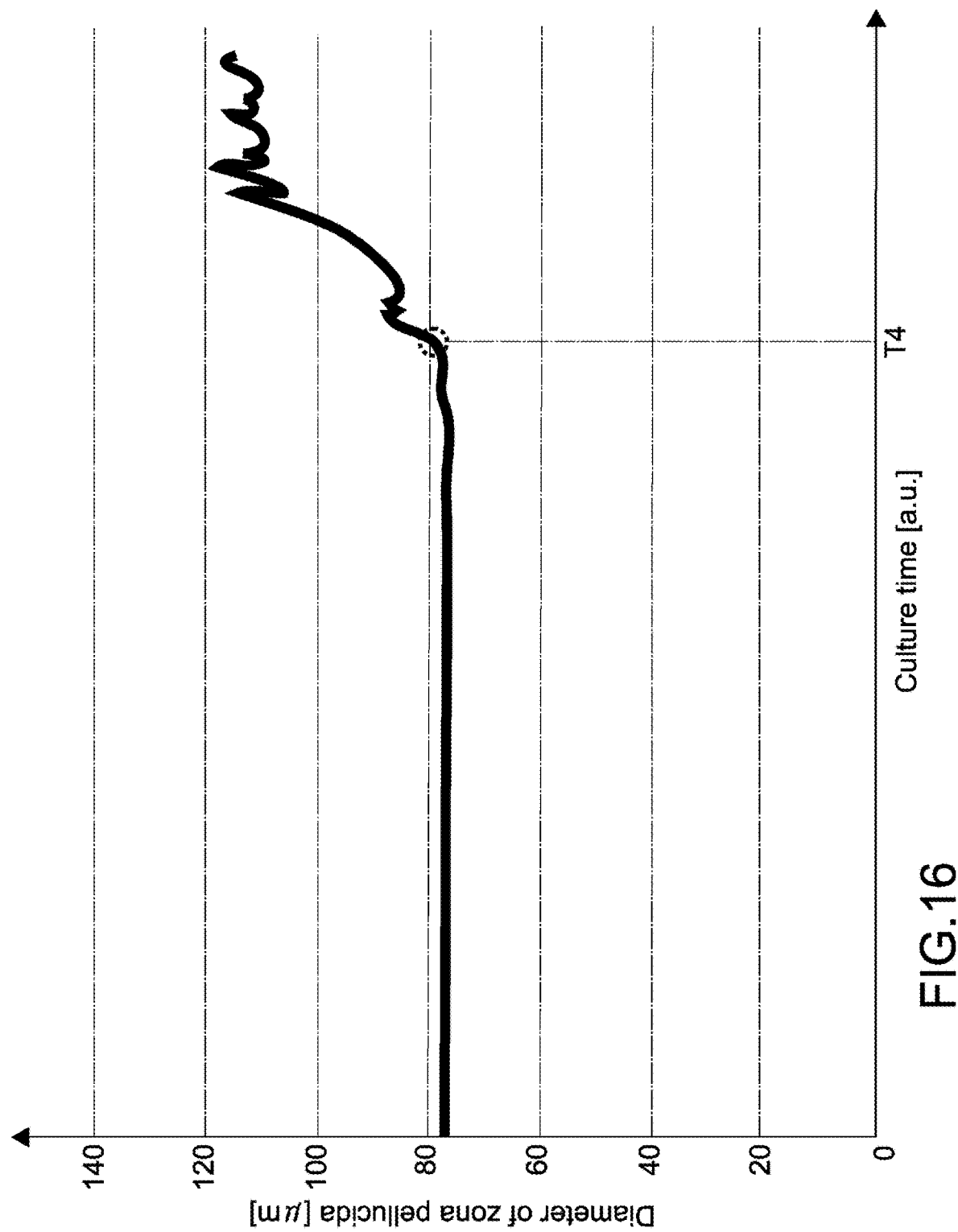
FIG. 16 is a diagram schematically showing the graph, which visualizes time-series transformation of the fertile ovum of this embodiment.

FIG. 16 is a graph showing time-series change of the diameter the zona pellucida with respect to the culture time. The determining unit 56 analyzes the numerical data about the transformation (change of the diameter of the zona pellucida) output from the feature amount calculating unit 54 in a predetermined way, and thereby detects a culture time T4 when change of the diameter of the zona pellucida per unit culture time is larger than 0.

Subsequently, the determining unit 56 determines that the growth state of the fertile ovum F at the culture time T4 is an expanding blastocyst state. Therefore, it is possible to quantitatively and objectively know the time and the like when the growth state of the fertile ovum F is changed to an expanding blastocyst state. Note that the determining unit 56 may also determine that the growth state of the fertile ovum F is an expanding blastocyst state on the basis of not only the time-series change of the diameter of the zona pellucida but also at least one of the time-series change of the area of the zona pellucida and the time-series change of the thickness of the zona pellucida.

(Step S07: Calculate Predictive Value)

The predicting unit 57 checks at least one of the numerical data about the transformation and the numerical data about the feature amount, which are output from the feature amount calculating unit 54, against third quality data corresponding thereto (incubation rate, implantation rate, pregnancy rate, conception rate, miscarriage rate, birthweight, birth rate, and breeding value of a grown-up, etc.) prestored in the fertile ovum information database 59. As a result, the predicting unit 57 calculates at least one of an incubation rate, an implantation rate, a pregnancy rate, a conception rate, a miscarriage rate, a birthweight, a birth rate, and a breeding value of a grown-up of the fertile ovum F.

At this time, the predicting unit 57 selects, as the third quality data corresponding to the numerical data about the transformation and the numerical data about the feature amount output from the feature amount calculating unit 54, the third quality data about the fertile ovum F having the transformation and the feature amount most similar thereto. The predicting unit 57 retrieves the selected third quality data from the fertile ovum information database 59.

Next, the predicting unit 57 outputs the predictive value of the fertile ovum F, which is determined by checking at least one of the numerical data about the transformation and the numerical data about the feature amount against the third quality data, to the display controller unit 58 and the fertile ovum information database 59. As a result, the predictive value is stored as new reference data (third quality data) in the fertile ovum information database 59, and the fertile ovum information database 59 is updated.

(Step S08: Display Quality Result)

The display controller unit 58 displays, on the display device 60, a web dashboard indicating the first and second time-series images G1 and G2 (original images) obtained from the image obtaining unit 51 and the image processing unit 52, the processed images obtained from the recognizing unit 53 (fertile-ovum-recognized images, motion vector images, heat map image indicating motion amounts, and the like), the transformation and the feature amount obtained from the feature amount calculating unit 54, the quality result of the fertile ovum F obtained from the determining unit 56, the predictive value obtained from the predicting unit 57, a quality code corresponding to a growth state of the fertile ovum F, alternatively, various images and quality information retrieved from the fertile ovum information database 59, and the like.

As a result, a user may select the fertile ovum F before implantation with a high degree of accuracy comprehensively in view of the images under observation, the fertile-ovum-recognized image, the motion vector image, the heat map image indicating movement amounts, the transformation, the feature amount, the quality result, the predictive value, and the like about the fertile ovum F. Note that the display controller unit 58 may display, on the display device 60, not only the above-mentioned information but also position information of the well W in which the fertile ovum F is held, image-capture date and time, image-capture conditions, and the like.

(Machine Learning Algorithm)

In the present technique, the information processing apparatus 100 executes the above-mentioned steps including Step S02 to Step S07 in accordance with a machine learning algorithm. The machine learning algorithm is not particularly limited. For example, a machine learning algorithm that employs a neural network such as RNN (Recurrent Neural Network), CNN (Convolutional Neural Network), and MLP (Multilayer Perceptron) may be used. Alternatively, an arbitrary machine learning algorithm that executes supervised learning, unsupervised learning, semi-supervised learning, reinforcement learning, or other learning may be used.

(Effects)

In recent years, in the fertility treatment field, the livestock industrial field, and other fields, the quality of a cell (fertile ovum) to be implanted is an important factor that affects implantation results. Typically, a cell to be implanted is selected by determining the growth or quality of a cell on the basis of morphological findings by using an optical microscope, an image processing apparatus, or the like.

However, the above-mentioned morphological evaluation method of evaluating the quality of a fertile ovum before implantation requires a skilled person. In addition, a person tends to be subjective. In view of such circumstances, it is required to provide a method of assisting the evaluation of the quality of a fertile ovum quantitatively and highly objectively. It is required to provide a method of assisting the evaluation of the quality of a fertile ovum not only morphologically but also multilaterally.

In view of the above-mentioned circumstances, according to the present embodiment, the information processing apparatus 100 assists in the evaluation of the quality of the fertile ovum F before implantation by using the quality information, in which the feature amount based on the transformation of the fertile ovum F is in association with the quality result of the fertile ovum F obtained on the basis of morphological findings. Therefore the quality of the fertile ovum F may be multilaterally evaluated in view of morphological findings of the fertile ovum F and the transformation of the fertile ovum F. The fertile ova F under observation may then be evaluated with a high degree of accuracy.

Further, according to the present embodiment, the information processing apparatus 100 is capable of automatically calculating the transformation, the feature amount, and the like about the fertile ovum F on the basis of images of the fertile ovum F. Therefore efficiency of evaluation of the quality of the fertile ovum F multilaterally is greatly increased as compared to evaluation in the past, in which an embryologist confirms images of a fertile ovum F one by one on the basis of his/her morphological findings.

(Modification Examples)

In the first embodiment, the determining unit 56 determines the quality, the growth state, and the like of the fertile ovum F by checking the numerical data about the transformation or the numerical data about the feature amount against the fourth quality data. However, other than the above, the second quality data may be used.

Second Embodiment

Next, with reference to FIG. 7 as necessary, a method of evaluating the quality of the fertile ovum F executed by an information processing apparatus 100 according to a second embodiment of the present technique will be described. The information processing apparatus 100 of the present embodiment is capable of executing the following steps in addition to, or instead of, the above-mentioned evaluation method of the first embodiment. Note that description of steps similar to the steps of the first embodiment will be omitted. In other words, the second embodiment may be carried out in addition to, or as an alternative to, the first embodiment.

(Step S04: Calculate Transformation)

Figure 17:
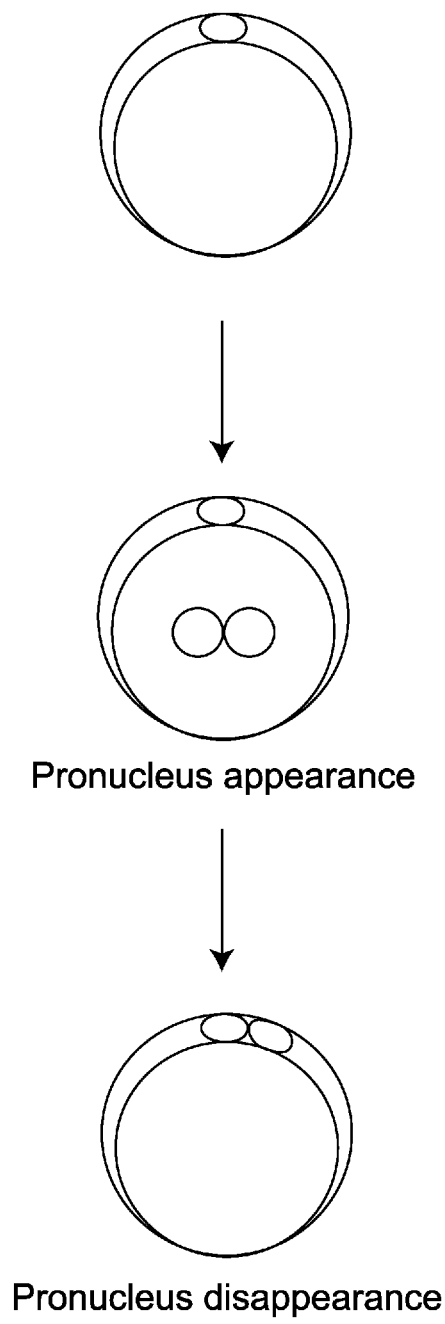
FIG. 17 is a diagram schematically showing appearance and disappearance of a pronucleus in the growth process of the fertile ovum.

FIG. 17 is a diagram schematically showing appearance and disappearance of a pronucleus in the growth process of a typical fertile ovum. As shown in FIG. 17, two pronuclei (2PN), i.e., a male pronucleus derived from a spermatozoon and a female pronucleus derived from an egg can be confirmed in a normal fertile ovum. The two pronuclei are known to bind firmly together and disappear in approximately 22 hours after fertilization. Meanwhile, the fertile ovum F has only one pronucleus (1PN) in some cases because the male pronucleus and the female pronucleus are on the way to binding firmly together to disappear. Alternatively, the fertile ovum F has only one pronucleus (1PN) in some cases due to abnormal fertilization. Further, the fertile ovum has three or more pronuclei (not less than 3PN) in some cases, which is called multi-pronuclei. There is a high possibility that an abnormality such as a chromosomal abnormality has occurred in such a fertile ovum.

Figure 20:
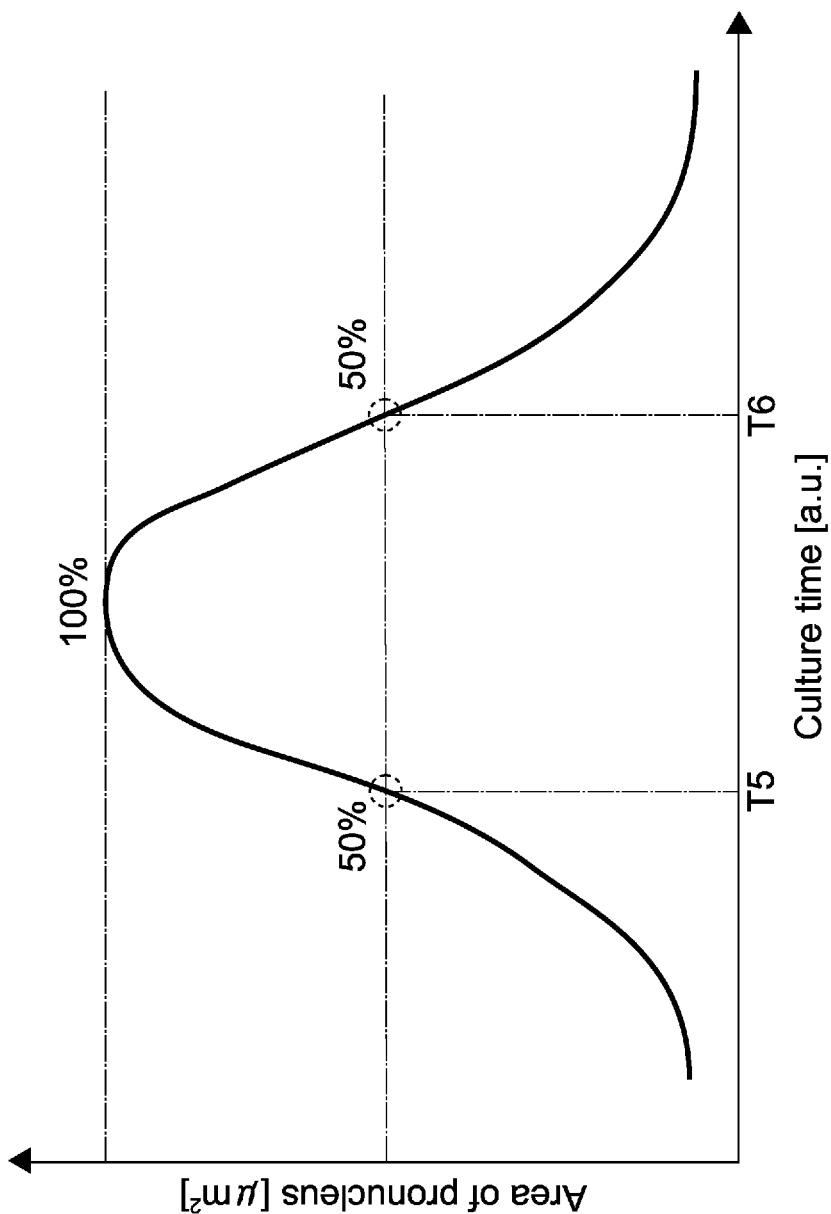
FIG. 20 is a diagram schematically showing the graph, which visualizes time-series transformation of the fertile ovum of this embodiment.

In the present embodiment, the feature amount calculating unit 54 calculates, as the transformation, change of the area of each of the pronuclei (see FIG. 20). As a result, it is possible to determine appearance time and disappearance time of the pronucleus in the growth process of the fertile ovum F.

(Step S05: Calculate Feature Amount)

Figure 18:
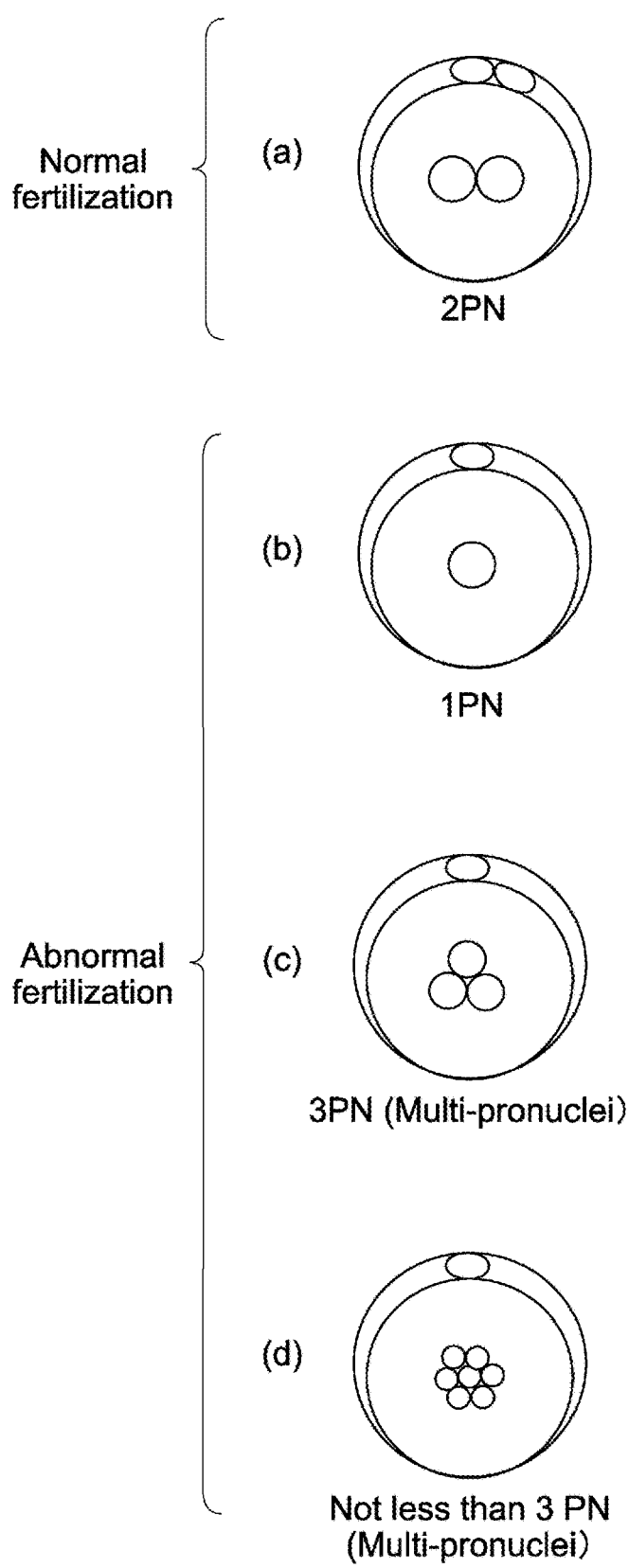
FIG. 18 is a diagram schematically showing various fertile ova having different number of pronuclei.
Figure 19:
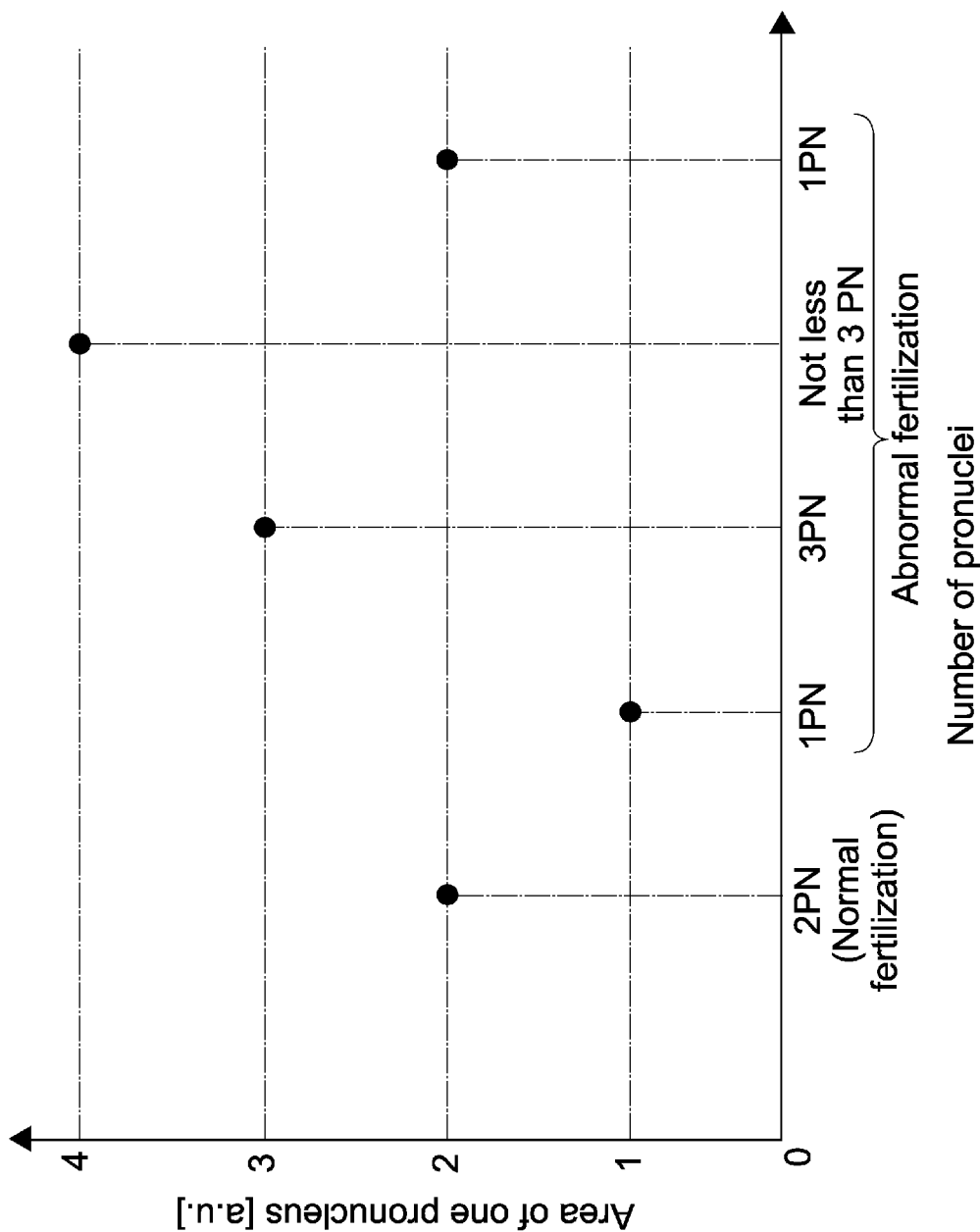
FIG. 19 is a graph showing a relationship between the area of the pronucleus of the fertile ovum and the number of pronuclei in a second embodiment of the present technique.

FIG. 18 is a diagram schematically showing various fertile ova having different number of pronuclei. FIG. 19 is a graph showing a relationship between the area of the pronucleus and the number of pronuclei. The feature amount calculating unit 54 calculates, as the feature amount, the number of pronuclei of the fertile ovum F on the basis of the area of the pronucleus calculated in the above-mentioned Step S04. As a result, as shown in FIG. 18, it is possible to determine whether or not the pronuclei of the fertile ovum F is abnormal on the basis of the number of pronuclei. In other words, it is possible to determine whether or not the fertile ovum F is normally fertilized and the type of abnormal fertilization.

(Step S06: Determine Quality)

FIG. 20 is a graph showing time-series change of the area of the pronucleus with reference to the culture time. Where the feature amount calculating unit 54 calculates, as the transformation, change of the area of the pronucleus in the above-mentioned Step S04, the determining unit 56 determines an appearance time T5 and a disappearance time T6 of the pronucleus in the growth process of the fertile ovum F on the basis of change of the area of the pronucleus. As a result, it is possible to quantitatively and objectively know the appearance time T5 and the disappearance time T6 of the pronucleus of the fertile ovum F.

In the present embodiment, for example, the time when the area of the pronucleus is increased to 50% of the whole area from the culture start time is the appearance time T5 of the pronucleus, and the time when the area of the pronucleus is reduced to 50% of the whole area is the disappearance time T6 of the pronucleus. In this case, it is favorable that the appearance time T5 is 6 to 18 hours after the culture start time, and the disappearance time T6 is 16 to 24 hours after the culture start time.

The determining unit 56 determines whether or not the pronucleus of the fertile ovum F is abnormal on the basis of the number of pronuclei calculated as the feature amount in the above-mentioned Step S05. At this time, as shown in FIG. 19, the determining unit 56 determines the type (1PN, 3PN, not less than 3PN) of the fertile ovum F having an abnormal pronucleus on the basis of the number of pronuclei confirmed by the morphological findings in the above-mentioned Step S02 and the number of pronuclei calculated as the feature amount. As a result, whether or not the fertile ovum F is normally fertilized and the type of abnormal fertilization are automatically determined.

Third Embodiment

Next, with reference to FIG. 7 as necessary, a method of evaluating the quality of the fertile ovum F where a polar body (PB) of the fertile ovum F is recognized executed by the information processing apparatus 100 according to a third embodiment of the present technique will be described. The information processing apparatus 100 of the present embodiment is capable of executing the following steps in addition to, or instead of, the above-mentioned evaluation method of the first and second embodiments. Note that description of steps similar to the steps of the first and second embodiments will be omitted. In other words, the third embodiment may be carried out in addition to, or as an alternative to, the first and/or second embodiment.

(Step S05: Calculate Feature Amount)

Figure 21:
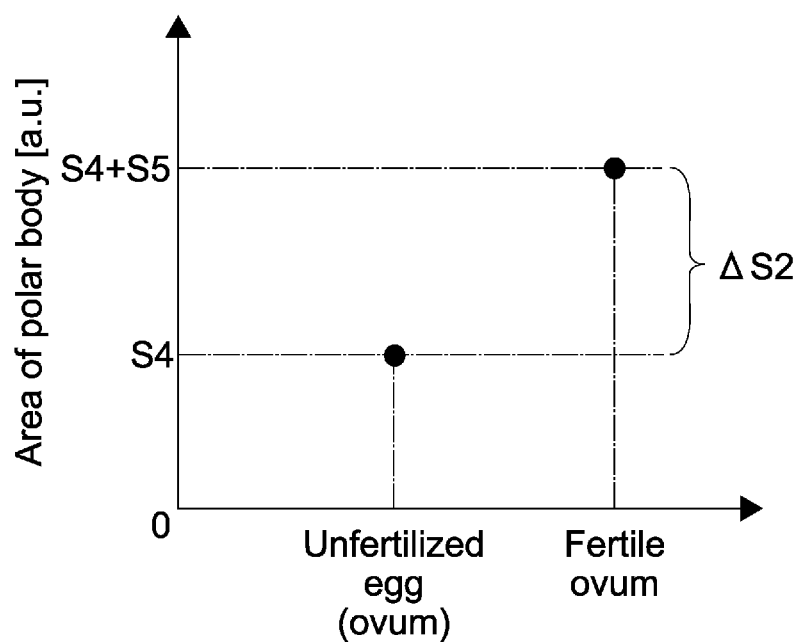
FIG. 21 is a graph showing a relationship between the area of a first polar body of an unfertilized ovum and the area of the polar body part of the fertile ovum derived from the unfertilized ovum in a third embodiment of the present technique.

FIG. 21 is a graph showing a relationship between the area of a first polar body of an unfertilized egg (ovum) and the area of the polar body part of the fertile ovum derived from the unfertilized ovum. Matured eggs each produce (form) a nucleus called a first polar body in perivitelline space of space between the zona pellucida and the plasma membrane. Such an egg produces (forms) a second polar body by cell division accompanying sperm entering. Therefore, whether or not the fertile ovum is normally fertilized may be determined on the basis of whether or not the second polar body is produced (formed).

The feature amount calculating unit 54 calculates an area S4 of the first polar body and an area S5 of the second polar body in the polar body part of the fertile ovum F recognized in the above-mentioned Step S03. Subsequently, the feature amount calculating unit 54 calculates, as the feature amount, the number of polar bodies of the fertile ovum F on the basis of a difference ((S4+S5)−S4) between a sum (S4+S5) of the areas of the first polar body and the second polar body and the area S4 of the first polar body at the time when the fertile ovum F is in a state of an unfertilized ovum (egg). As a result, as shown in FIG. 21, it is possible to determine whether or not the second polar body is produced by the fertile ovum F after fertilization in accordance with the presence/absence of the difference (ΔS2). In other words, it is possible to determine whether or not the fertile ovum F is normally fertilized.

(Step S06: Determine Quality)

Figure 22:
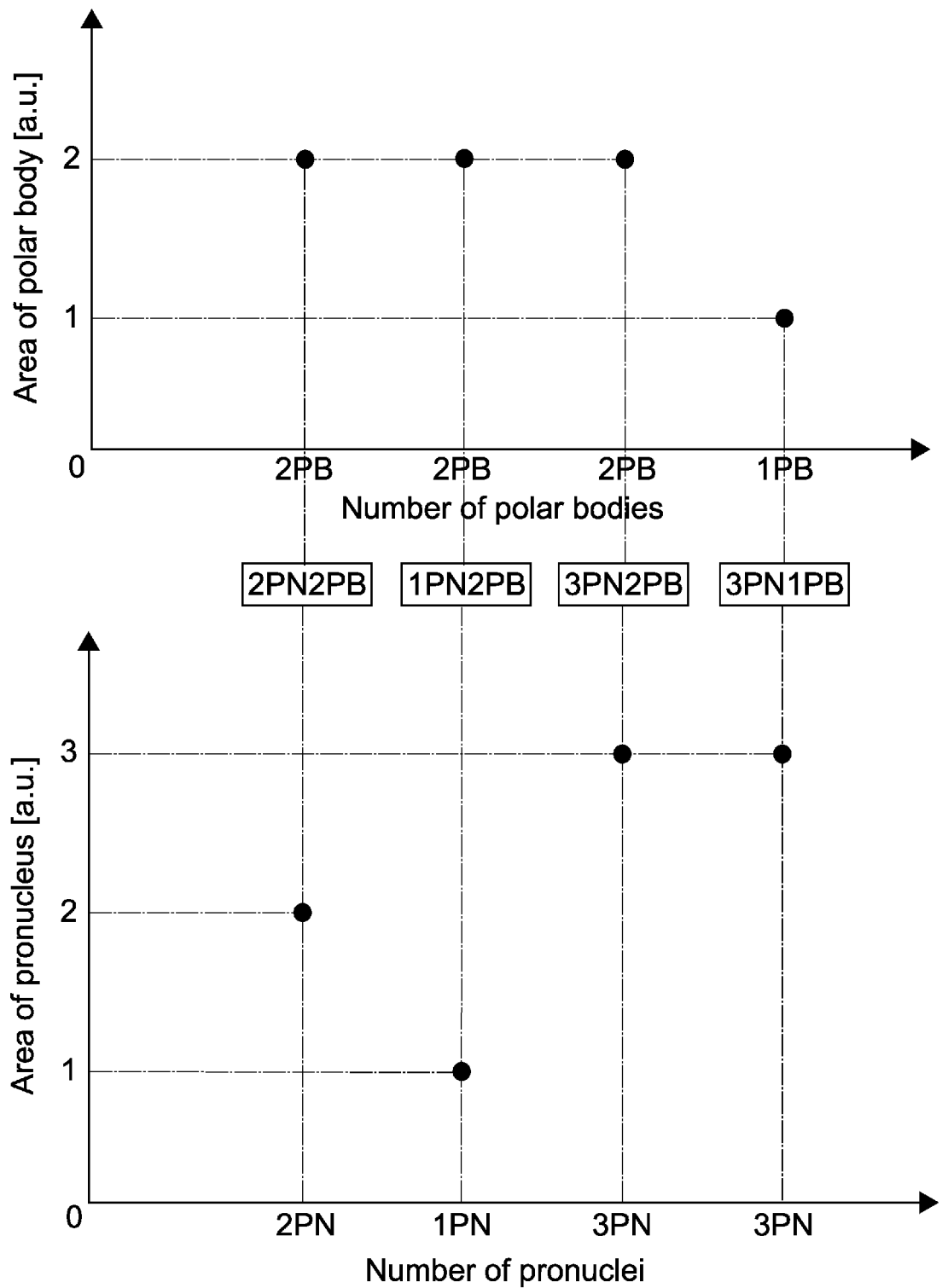
FIG. 22 is a diagram showing both the graph, which shows a relationship between the area of the pronucleus and the number of pronuclei, and the graph, which shows a relationship between the area of the polar body and the number of polar bodies, in the third embodiment.

FIG. 22 is a diagram showing both the graph, which shows a relationship between the area of the pronucleus and the number of pronuclei, and the graph, which shows a relationship between the area of the polar body and the number of polar bodies. The determining unit 56 determines whether or not the polar body of the fertile ovum F is abnormal on the basis of the number of polar bodies calculated as the feature amount in the above-mentioned Step S05. Specifically, as shown in FIG. 22, the determining unit 56 determines that the form of the fertile ovum F is 2 pronuclei and 2 polar bodies (2PN2PB), 1 pronucleus and 2 polar bodies (1PN2PB), 3 pronuclei and 2 polar bodies (3PN2PB), or 3 pronuclei and 1 polar body (3PN1PB) on the basis of the number of pronuclei calculated as the feature amount in the second embodiment, and the number of polar bodies.

As a result, not only whether or not the fertile ovum F is normally fertilized but also the type of abnormal fertilization are automatically determined. Note that according to the current biological findings, the form of the fertile ovum of 2 pronuclei and 2 polar bodies corresponds to normal fertilization, and the form of the fertile ovum of 1 pronucleus and 2 polar bodies (1PN2PB), 3 pronuclei and 2 polar bodies (3PN2PB), or 3 pronuclei and 1 polar body (3PN1PB) corresponds to abnormal fertilization.

Fourth Embodiment

Next, with reference to FIG. 7 as necessary, a method of evaluating the quality of the fertile ovum F where a nucleus in a blastomere of the fertile ovum F is recognized executed by the information processing apparatus 100 according to a fourth embodiment of the present technique will be described. The information processing apparatus 100 of the present embodiment is capable of executing the following steps in addition to, or instead of, the above-mentioned evaluation method of the first to third embodiments. Note that description of steps similar to the steps of the first to third embodiments will be omitted. In other words, the fourth embodiment may be carried out in addition to, or as an alternative to, any one of the first to third embodiments.

(Step S05: Calculate Feature Amount)

Figure 23:
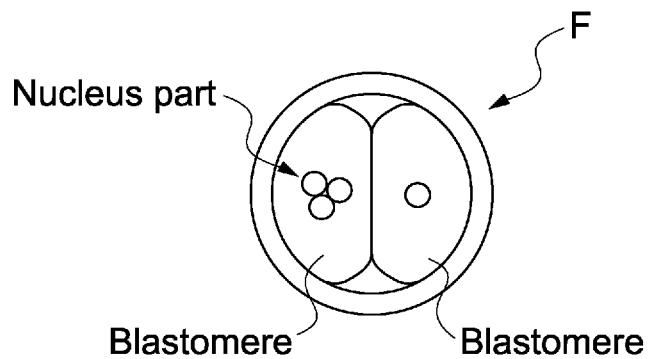
FIG. 23 is a diagram schematically showing the two-cell stage fertile ovum of a fourth embodiment of the present technique.

FIG. 23 is a diagram schematically showing the two-cell stage fertile ovum F. The feature amount calculating unit 54 calculates the area of a nucleus part in a blastomere of the fertile ovum F recognized in the above-mentioned Step S03. Subsequently, the feature amount calculating unit 54 calculates, as the feature amount, the number of nuclei in the blastomere of the fertile ovum F on the basis of the area of the nucleus part. As a result, it is possible to determine whether or not the blastomere of the fertile ova F is in a polynuclear state.

(Step S06: Determine Quality)

Figure 24:
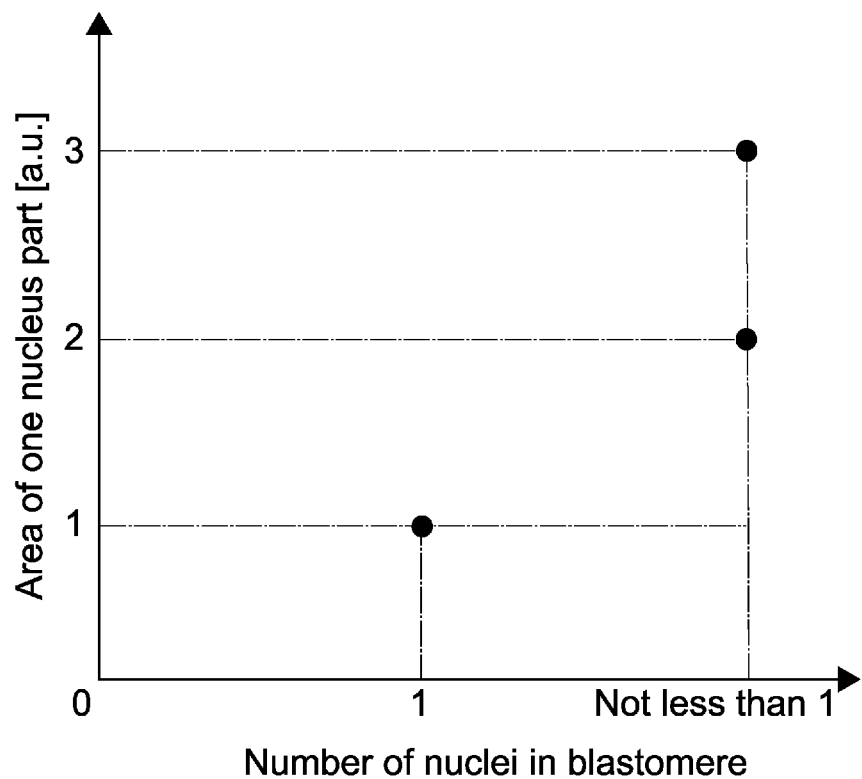
FIG. 24 is a graph showing a relationship between the area of the nucleus part in blastomeres of the fertile ovum and the number of nuclei in the blastomeres in this embodiment.

FIG. 24 is a graph showing a relationship between the area of the nucleus part in the blastomeres of the fertile ovum F and the number of nuclei in the blastomeres. The determining unit 56 determines whether or not the blastomere of the fertile ovum F is in a polynuclear state on the basis of the number of nuclei in the blastomere calculated as the feature amount in the above-mentioned Step S05. At this time, the determining unit 56 determines whether or not the blastomere is in a polynuclear state on the basis of the number of nuclei in the blastomere confirmed by the morphological findings in the above-mentioned Step S02, and the number of nuclei in the blastomere calculated as the feature amount. As a result, for example, in the growth stage of the fertile ovum F from the two-cell stage to the morula stage, whether or not the blastomere is in a polynuclear state is automatically determined.

Fifth Embodiment

Next, with reference to FIG. 7 as necessary, a method of evaluating the quality of the fertile ovum F where fragmentation of the fertile ovum F is recognized executed by the information processing apparatus 100 according to a fifth embodiment of the present technique will be described. The information processing apparatus 100 of the present embodiment is capable of executing the following steps in addition to, or instead of, the above-mentioned evaluation method of the first to fourth embodiments. Note that description of steps similar to the steps of the first to fourth embodiments will be omitted. In other words, the fifth embodiment may be carried out in addition to, or as an alternative to, any one of the first to fourth embodiments.

(Step S05: Calculate Feature Amount)

Figure 25:
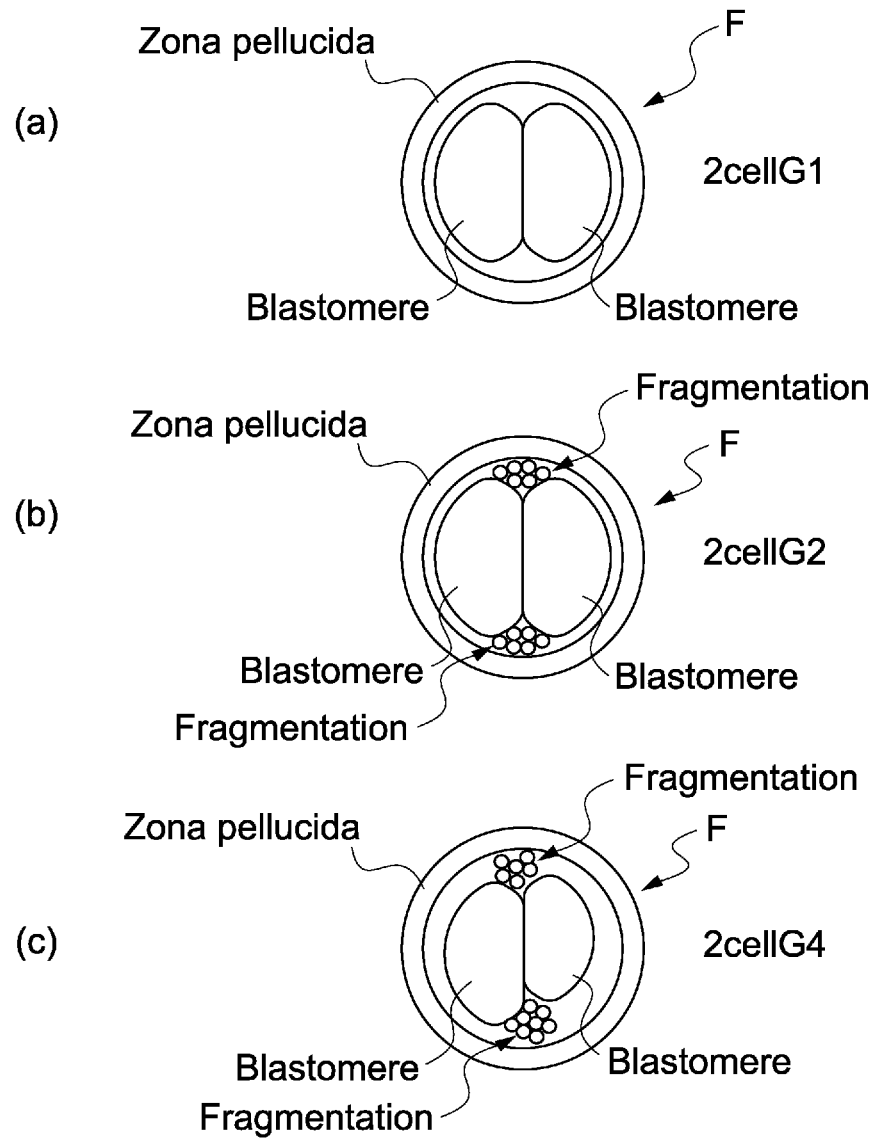
FIG. 25 is a diagram schematically showing various two-cell stage fertile ova F whose qualities are graded in a fifth embodiment of the present technique.
Figure 26:
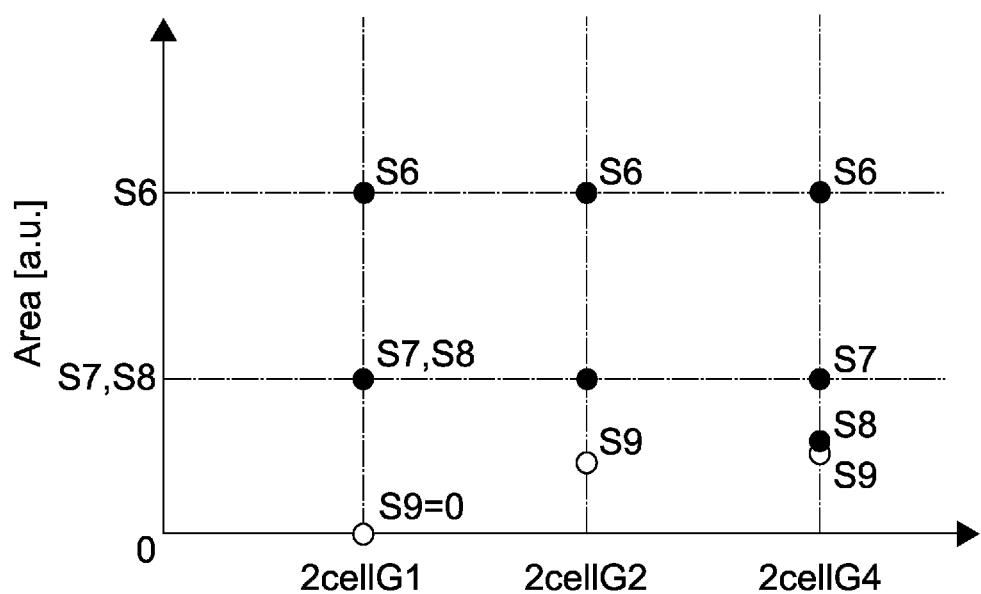
FIG. 26 is a graph showing the area of the fragmentation, the area of the zona pellucida, and the area of the blastomeres of the fertile ova in the respective grades in this embodiment.

FIG. 25 is a diagram schematically showing various two-cell stage fertile ova F whose qualities are graded. FIG. 26 is a graph showing the area of the fragmentation, the area of the zona pellucida, and the area of the blastomere of the fertile ova F in the respective grades in this embodiment.

In the past, for example, Veeck's classification is often used to evaluate the quality of the 4 to 8-cell stage fertile ovum. In the Veeck's classification, the quality of the fertile ovum is graded to five stages (G1 to G5) depending on whether cell-division is clearly performed in the growth process of the fertile ovum or whether the amount of fragmentation (cell fragments generated when the fertile ovum undergoes cell-division) is large or small. This grade is an important indicator in selecting a fertile ovum, which is predicted to have a high genesis ability. Note that in the Veeck's classification, the fertile ovum is evaluated as one with higher quality in the order of Grade 5 to Grade 1.

In the present embodiment, as shown in FIG. 26, the feature amount calculating unit 54 calculates an area S9 of the fragmentation and an area S6 of the zona pellucida of the fertile ovum F recognized in the above-mentioned Step S03, and areas S7 and S8 of cells (blastomeres) in the fertile ovum F.

Subsequently, the feature amount calculating unit 54 calculates, as the feature amount, the proportion of the area of the fragmentation to the sum of the areas of the zona pellucida and the blastomeres. In the present embodiment, it is favorable that the proportion of the area is not more than 10% where a plurality of blastomeres are uniform (see (b) of FIG. 25), and not less than 10% and not more than 50% where the plurality of blastomeres are not uniform (see (c) of FIG. 25).

(Step S06: Determine Quality)

The determining unit 56 grades the quality of the fertile ovum F on the basis of the proportion of the area (S9) of the fragmentation to the sum (S6+S7+S8) of the areas of the zona pellucida and the blastomeres calculated as the feature amount in the above-mentioned Step S05.

Therefore, the grading operation as described in the above-mentioned Step S05, which has been performed on the basis of morphological findings, is automated, and the operation efficiency in selecting the fertile ovum F, which is predicted to have a high genesis ability before implantation, is significantly improved.

Sixth Embodiment

Next, with reference to FIG. 7 as necessary, a method of evaluating the quality of the fertile ovum F where Halo of the fertile ovum F is recognized executed by the information processing apparatus 100 according to a sixth embodiment of the present technique will be described. The information processing apparatus 100 of the present embodiment is capable of executing the following steps in addition to, or instead of, the above-mentioned evaluation method of the first to fifth embodiments. Note that description of steps similar to the steps of the first to fifth embodiments will be omitted. In other words, the sixth embodiment may be carried out in addition to, or as an alternative to, any one of the first to fifth embodiments.

(Step S04: Calculate Transformation)

Figure 27:
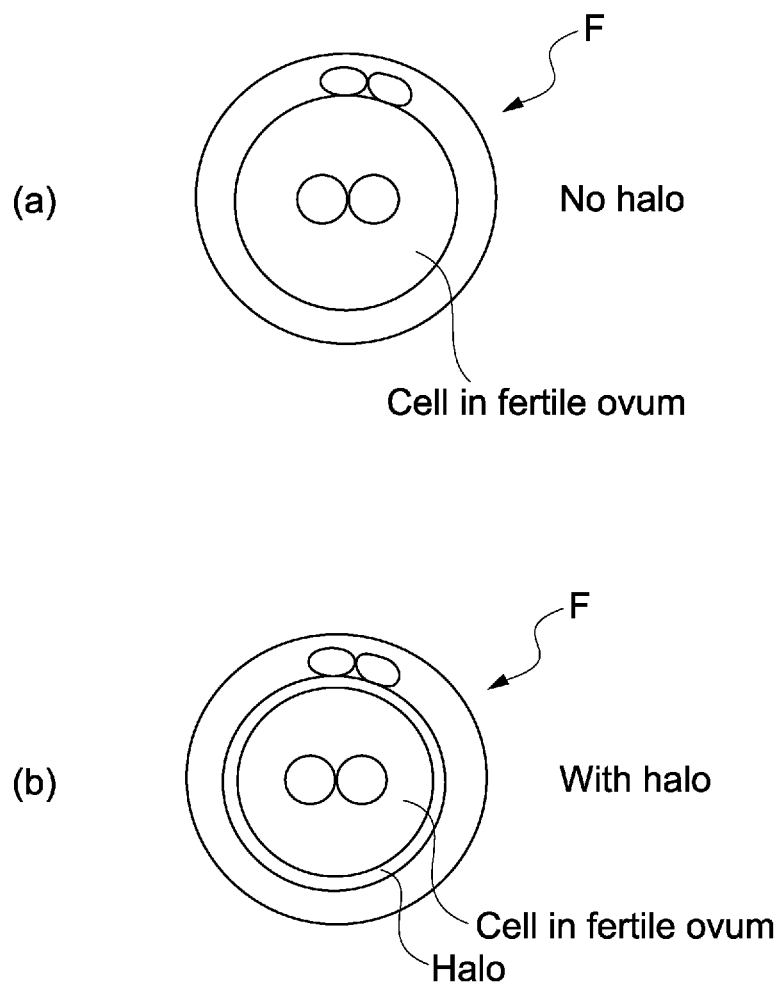
FIG. 27 is a diagram schematically showing the fertile ovum of a sixth embodiment of the present technique.

FIG. 27 is a diagram schematically showing the fertile ova F. (a) of FIG. 27 is a diagram schematically showing the fertile ovum F with no Halo, and (b) of FIG. 27 is a diagram schematically showing the fertile ovum F with Halo. The feature amount calculating unit 54 calculates an area S11 of the Halo of the fertile ovum F recognized in the above-mentioned Step S03. The feature amount calculating unit 54 calculates, as the transformation, time-series change of a proportion (S11/S10) of the area S11 of the Halo to the area S10 of the cells in the fertile ovum F. As a result, it is possible to determine appearance time and disappearance time of the Halo in the growth process of the fertile ovum F.

(Step S06: Determine Quality)

Figure 28:
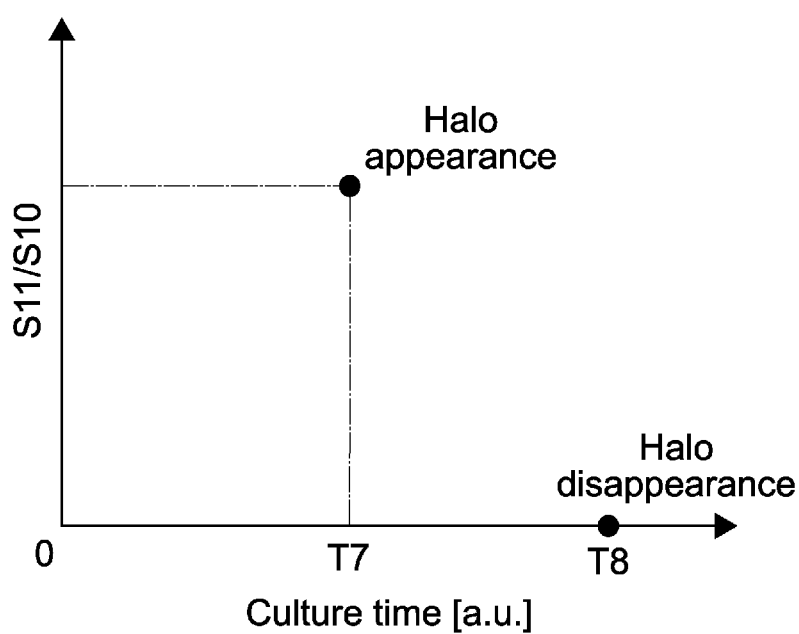
FIG. 28 is a graph obtained by plotting the proportion of the area of Halo to the area of cells in the fertile ovum of this embodiment in time series.

FIG. 28 is a graph obtained by plotting the proportion (S11/S10) of the area S11 of Halo to the area S10 of cells in the fertile ovum F in time series. As shown in FIG. 28, the determining unit 56 determines a appearance time T7 and a disappearance time T8 of the Halo in the growth process of the fertile ovum F on the basis of change of the proportion (S11/S10) of the area S11 of the Halo to the area S10 of the cells in the fertile ovum F calculated as the transformation in the above-mentioned Step S04. As a result, the appearance time T7 and the disappearance time T8 of the Halo of the fertile ovum F are automatically determined.

In the present embodiment, for example, in the growth process of the fertile ovum F, the time when S11/S10 is confirmed first from the culture start time is the appearance time T7 of the Halo, and the time when S11/S10 becomes zero after S11/S10 is confirmed is the disappearance time T8 of the Halo.

Seventh Embodiment

Next, with reference to FIG. 7 as necessary, a method of evaluating the quality of the fertile ovum F executed by the information processing apparatus 100 according to a seventh embodiment of the present technique will be described. The information processing apparatus 100 of the present embodiment is capable of executing the following steps in addition to, or instead of, the above-mentioned evaluation method of the first to sixth embodiments. Note that description of steps similar to the steps of the first to sixth embodiments will be omitted. In other words, the seventh embodiment may be carried out in addition to, or as an alternative to, any one of the first to sixth embodiments.

(Step S04: Calculate Transformation)

The feature amount calculating unit 54 analyzes the plurality of overlay images G6 output from the recognizing unit 53 in a predetermined way, and thereby calculates time-series change of a macroscopic inner motion amount of the fertile ovum F. The feature amount calculating unit 54 outputs numerical data about the change of the motion amount to the image-capture controller unit 55, the determining unit 56, the predicting unit 57, the display controller unit 58, and the fertile ovum information database 59. The numerical data output to the fertile ovum information database 59 is stored in the fertile ovum information database 59, and treated as reference data.

The feature amount calculating unit 54 calculates a differential value between the mask area of one overlay image and the mask area of another overlay image of the plurality of mask areas formed on the plurality of overlay images G6 in the above-mentioned Step S03. In other words, the feature amount calculating unit 54 calculates inter-frame differential values of only the mask areas along the cells of the fertile ovum F, and calculates the change of the motion amount on the basis of the differential value.

As a result, occurrence of noises and mis-detection, which results from an interframe differential value calculated on the basis of the whole captured images of the fertile ovum F, is reduced. The change of an inner motion amount of the fertile ovum F may be calculated accurately.

Figure 29:
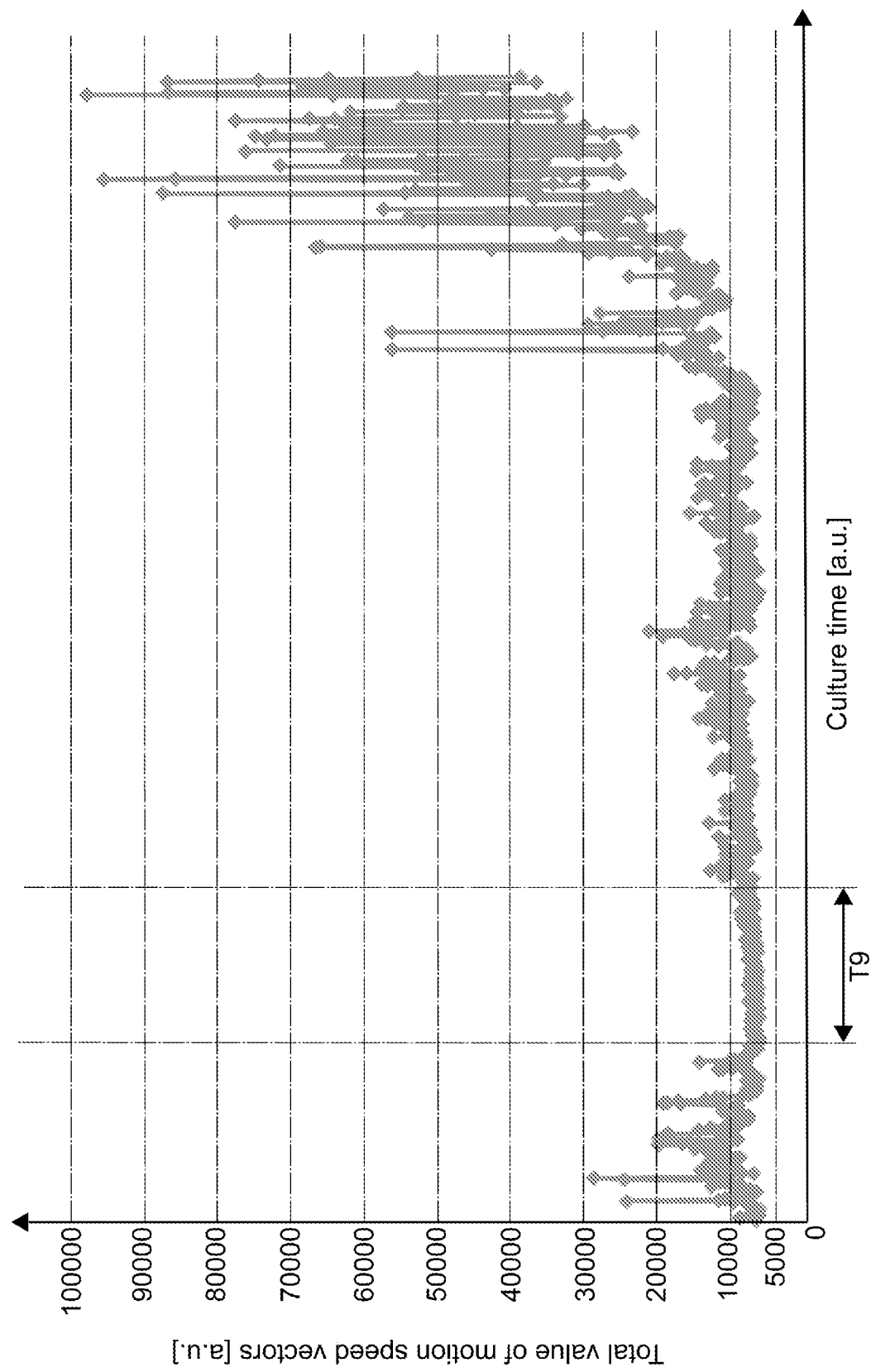
FIG. 29 is a graph, which visualizes the time-series change of the motion amount of the inside of the fertile ovum of a seventh embodiment of the present technique.
Figure 30:
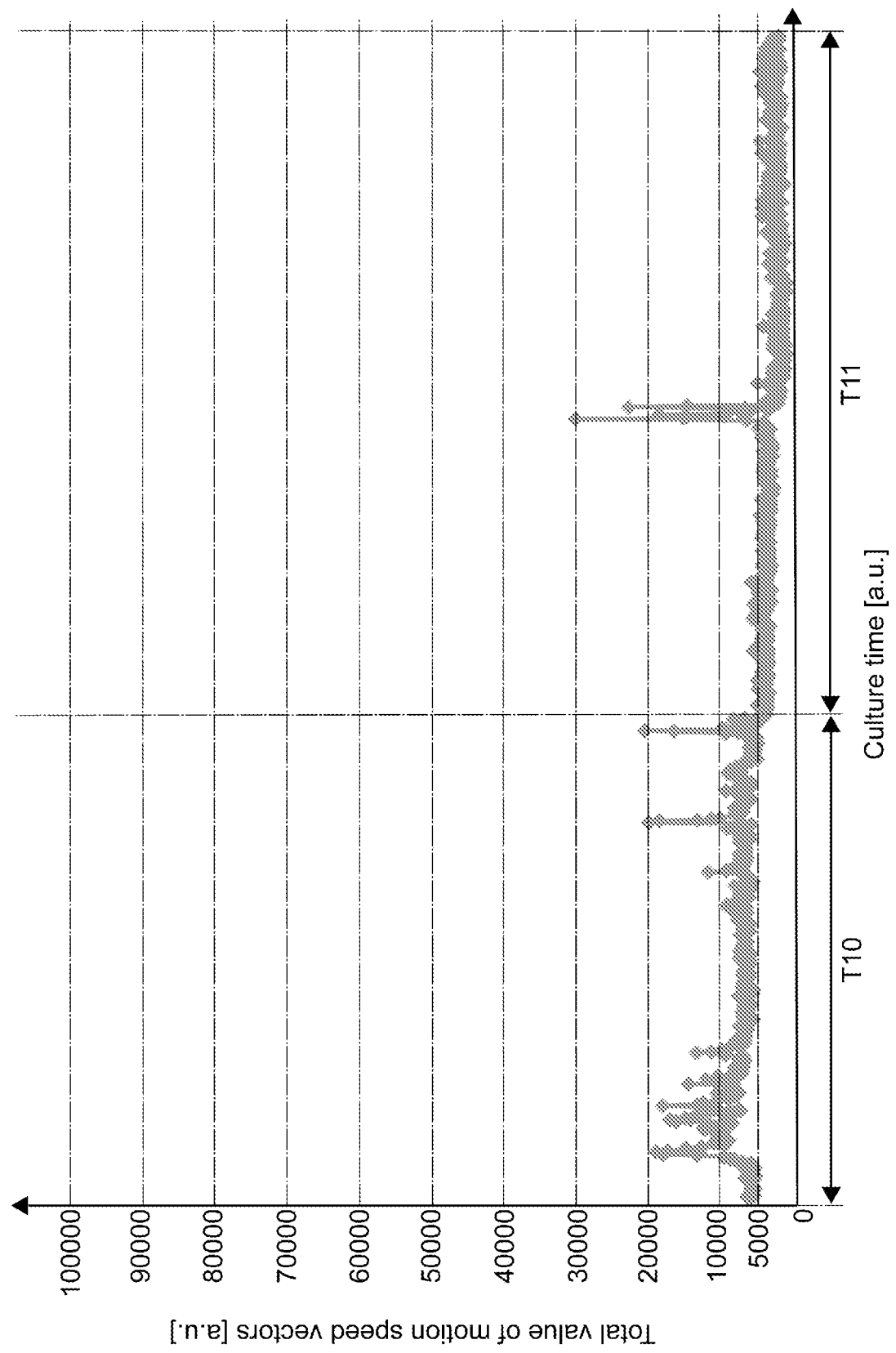
FIG. 30 is a graph, which visualizes the time-series change of the motion amount of the inside of the fertile ovum of this embodiment.
Figure 31:
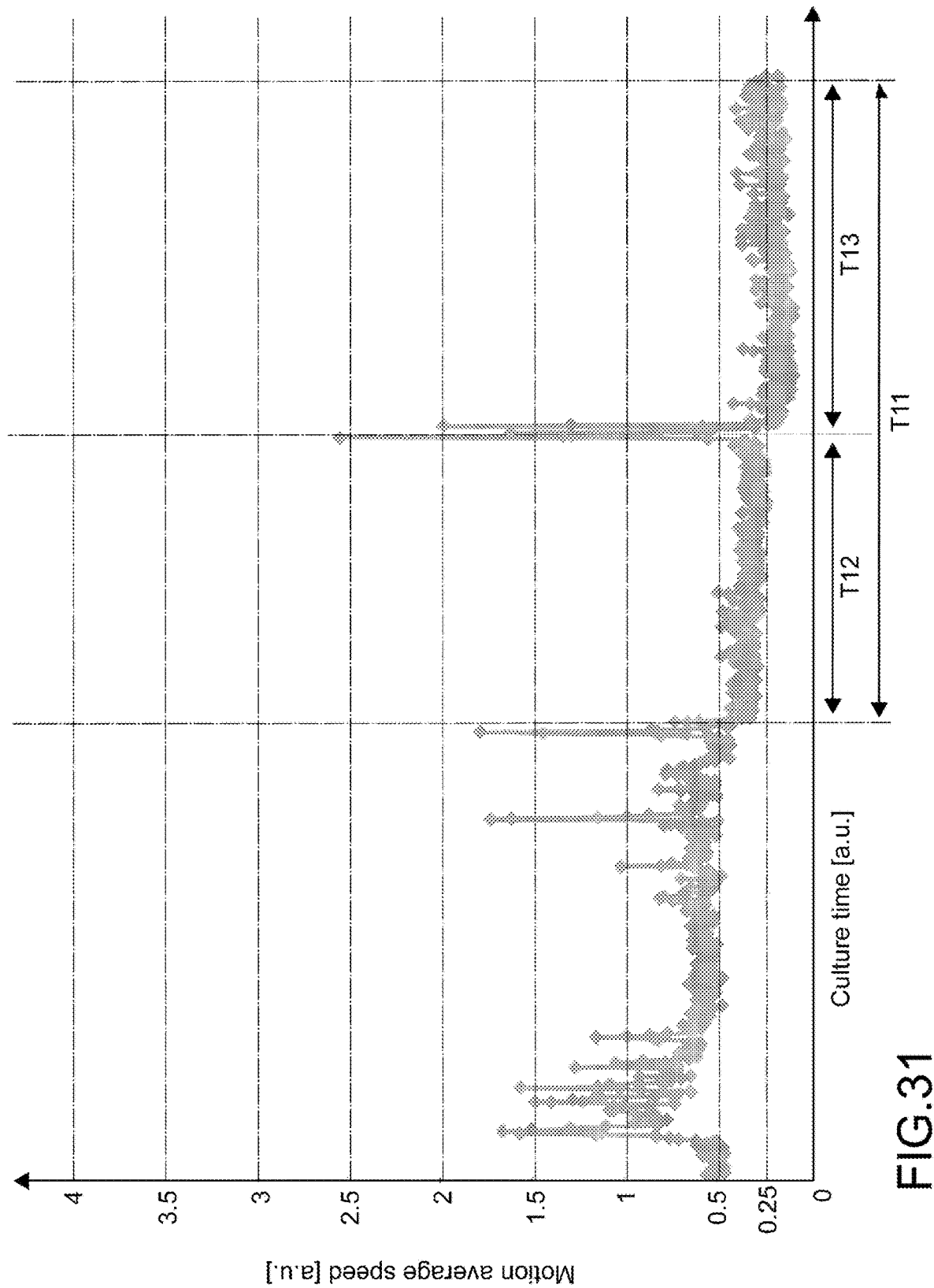
FIG. 31 is a graph, which visualizes the time-series change of the motion amount of the inside of the fertile ovum of this embodiment.

FIGS. 29 to 31 are each a graph showing the change of a motion amount of the cells inside the fertile ovum F with reference to the culture time. The feature amount calculating unit 54 calculates, as the change of the motion amount, time-series change of at least one of the minimum speed of motion vectors of the cells, the maximum speed, the maximum acceleration, the average speed, the average acceleration, the median value, the standard deviation, the total value of motion speed vectors, and the total value of motion acceleration vectors. Therefore, since they are visualized as shown in the graphs of FIGS. 29 to 31 or the like, it is possible to evaluate the motion ability of the inside of the fertile ovum F where the outline of the fertile ovum F less changes.

(Step S06: Determine Quality)

The determining unit 56 analyzes the numerical data about the time-series change of a total value of motion speed vectors output from the feature amount calculating unit 54 in a predetermined way, and thereby detects a time period T9 when the total value of the motion speed vectors is greater than, for example, 5000, and change of the motion speed vectors per unit culture time is approximately zero.

Subsequently, for the fertile ovum F from which the time period T9 is detected, the determining unit 56 determines that a state of the fertile ovum F in the time period T9 is a lag-phase (cell inactive period). As a result, it is possible to automatically determine the lag-phase that is an indicator in selecting a fertile ovum, which is predicted to have a high genesis ability after implantation.

Further, the determining unit 56 of the present embodiment analyzes the numerical data about the time-series change of the total value of motion speed vectors of the fertile ovum F in a predetermined way, and thereby detects a time period T10 when the total value of motion speed vectors is greater than, for example, 5000, and change of the motion speed vectors per unit culture time is not zero. Further, the determining unit 56 detects a time period T11 when the total value of motion speed vectors is not more than, for example, 5000, and change of the motion speed vectors per unit culture time is approximately zero.

Subsequently, the determining unit 56 determines that the growth state of the fertile ovum F in the time period T10 is a degenerative cell proportion (proportion of degenerative cells to all the cells constituting the fertile ovum F) of less than 15%, and the growth state of the fertile ovum F in the time period T11 is a degenerative cell proportion of not less than 15%. At this time, a quality code depending on the growth state of the fertile ovum F is provided. For example, quality codes 1 and 2 are given to the growth state of the fertile ovum F in the time period T10, and quality codes 3 and 4 are given to the growth state of the fertile ovum F in the time period T11.

Further, the determining unit 56 retrieves, from the fertile ovum information database 59, the numerical data about the motion average speed of the fertile ovum F from which the time periods T10 and T11 are detected, analyzes the numerical data in a predetermined way, and thereby detects a time period T12, in which the motion average speed is larger than, for example 0.25, and a time period T13, in which the motion average speed is smaller than, for example 0.25, in the time period T11. Note that in the present embodiment, the unit of the motion average speed is, for example, "μm/s". However, the unit of the motion average speed may be appropriately changed depending on the number of pixels of an image on which the motion average speed of the fertile ovum F is displayed.

The determining unit 56 determines that the growth state of the fertile ovum F in the time period T12 is a degenerative cell proportion of not less than, for example, 15% and less than, for example, 50%, and the growth state of the fertile ovum F in the time period T13 is a degenerative cell proportion of not less than, for example, 50%. At this time, for example, the quality code 3 is given to the growth state of the fertile ovum F in the time period T12, and the quality code 4 is given to the growth state of the fertile ovum F in the time period T13.

According to the present embodiment, by detecting the time periods T9 to T13 regarding the time-series change of the motion amount of the cells in the fertile ovum F, it is possible to quantitatively and objectively know the state of the fertile ovum F as a degenerative cell proportion of less than, for example, 15%, not less than, for example, 15% and less than, for example, 50%, or not less than, for example, 50%, or as a lag-phase.

(Modification Examples)

In the seventh embodiment, the determining unit 56 determines the degenerative cell proportion and the lag-phase of the fertile ovum F on the basis of the time-series change of the total value of motion speed vectors or the time-series change of the motion average speed. Not limited to this, for example, the determining unit 56 may determine the degenerative cell proportion and the lag-phase on the basis of time-series change of the motion acceleration vector, the maximum speed, the maximum acceleration, the average acceleration, of the like of the cells in the fertile ovum F.

In this case, the determining unit 56 may detect a time period in which the total value of motion average speed is not less than, for example, 0.25, and the change of the motion average speed per unit culture time is approximately zero, and determine that the state of the fertile ovum F in the time period is the lag-phase.

Further, as the total value of motion speed vectors and the threshold value of the motion average speed, optimal values may be appropriately selected depending on the image-capture conditions, e.g., image-capture intervals and illumination conditions.

Embodiments of the present technique have been described above. However, the present technique is not limited to the above-mentioned embodiments and various modifications can be made without departing from the essence of the present technology.

For example, the observation system 100 repeats Step S01 at arbitrary intervals (for example, every predetermined time such as every 15 minutes or every 24 hours) or without interruption, and evaluates the quality of the fertile ovum F on the basis of images obtained in this step. Not limited to this, the observation system 100 of the present embodiment may obtain real-time images as necessary, and display the images of the fertile ovum F on the display device 60 to observe and evaluate the fertile ovum F as appropriate.

Further, according to the observation system 100 of the present technique, typically, the fertile ova F under observation are derived from cattle. Not limited to this, they may be derived from livestock such as mice, pigs, dogs, and cats, or may be derived from human.

Further, in the present description the term "fertile ovum" at least conceptually includes a single cell and a mass of a plurality of cells. Further, in the present specification, and applicable to all embodiments, a "cell" (singular) at least conceptually includes an individual cell and an aggregate of a plurality of cells. One or more "cells" as referred to herein relates to cells observed in one or more stages of embryonic development including, but not limited to, an oocyte, an egg (ovum), a fertile ovum (zygote), a blastocyst, and an embryo.

In addition, the present technology is applicable to arbitrary cells such as unfertilized egg cells (ova), embryos, or the like of animals in the livestock industrial field and other fields, and arbitrary cells such as biological samples obtained from living bodies such as stem cells, immune cells, and cancer cells in the regenerative medical field, the pathobiological field, the gene editing technique field, and other field.

Note that the present technique may employ the following configurations.

(1)

An information processing apparatus, including:

an image obtaining unit configured to obtain a plurality of original images of a fertile ovum captured in time series;

a recognizing unit including a probability image generating unit configured to generate probability images from the original images, the probability images each representing probability that the fertile ovum is present, the recognizing unit being configured to recognize the fertile ovum on the basis of the probability images; and a feature amount calculating unit configured to calculate time-series transformation of the fertile ovum from the probability images, and calculate a feature amount of the fertile ovum based on the transformation.

(2)

The information processing apparatus according to (1) above, in which the recognizing unit further includes a binarized image generating unit configured to generate binarized images from the probability images by processing the probability images by means of a binarizing process with a predetermined threshold value for each pixel, and is further configured to recognize the fertile ovum on the basis of the binarized images, and the feature amount calculating unit is further configured to calculate the time-series transformation of the fertile ovum from the binarized images, and calculate the feature amount of the fertile ovum based on the transformation.

(3)

The information processing apparatus according to (2) above, in which the recognizing unit further includes an overlay image generating unit configured to generate overlay images by overlaying the binarized images and the original images, and is further configured to recognize the fertile ovum on the basis of the overlay images, and the feature amount calculating unit is further configured to calculate the time-series transformation of the fertile ovum from the overlay images, and calculate the feature amount of the fertile ovum based on the transformation.

(4)

The information processing apparatus according to any one of (1) to (3) above, in which the recognizing unit is further configured to recognize a zona pellucida of the fertile ovum and a cell in the fertile ovum, and the feature amount calculating unit is further configured to calculate, as the transformation, change of an area of the zona pellucida and change of an area of the cell in the fertile ovum.

(5)

The information processing apparatus according to (4) above, in which the feature amount calculating unit is further configured to calculate, as the feature amount, at least one of compaction time of the fertile ovum and cleavage time of the fertile ovum on the basis of time-series change of the area of the zona pellucida and time-series change of the area of the cell in the fertile ovum.

(6)

The information processing apparatus according to (4) or (5) above, in which the recognizing unit is further configured to recognize a blastocyst as the cell in the fertile ovum, and the feature amount calculating unit is further configured to calculate, as the feature amount, at least one of a number of times of contraction, a contraction diameter, contraction speed, a contraction time period, contraction intervals, contraction strength, contraction frequency, a number of times of dilation, a dilation diameter, a dilation speed, a dilation time period, dilation intervals, dilation strength, and dilation frequency of the zona pellucida and the blastocyst on the basis of time-series change of a difference between the area of the zona pellucida and an area of the blastocyst.

(7)

The information processing apparatus according to any one of (1) to (6) above, in which the recognizing unit is further configured to recognize a zona pellucida of the fertile ovum, and the feature amount calculating unit is further configured to calculate, as the transformation, change of at least one of a diameter, an area, and a thickness of the zona pellucida.

(8)

The information processing apparatus according to any one of (1) to (7) above, in which the recognizing unit is further configured to recognize a pronucleus of the fertile ovum, and the feature amount calculating unit is further configured to calculate, as the transformation, change of an area of the pronucleus.

(9)

The information processing apparatus according to (8) above, in which the feature amount calculating unit is further configured to calculate, as the feature amount, a number of pronuclei on the basis of the area of the pronucleus.

(10)

The information processing apparatus according to any one of (1) to (9) above, in which the recognizing unit is further configured to recognize a first polar body and a second polar body of the fertile ovum, and the feature amount calculating unit is further configured to calculate, as the feature amount, a number of polar bodies of the fertile ovum on the basis of a difference between a sum of an area of the first polar body and an area of the second polar body and the area of the first polar body.

(11)

The information processing apparatus according to any one of (1) to (10) above, in which the recognizing unit is further configured to recognize a nucleus of a blastomere of the fertile ovum, and the feature amount calculating unit is further configured to calculate, as the feature amount, a number of nuclei on the basis of an area of the nucleus.

(12)

The information processing apparatus according to any one of (1) to (11) above, in which the recognizing unit is further configured to recognize a zona pellucida of the fertile ovum, a cell in the fertile ovum, and fragmentation of the fertile ovum, and the feature amount calculating unit is further configured to calculate, as the feature amount, a proportion of an area of the fragmentation to a sum of an area of the zona pellucida and an area of the cell in the fertile ovum.

(13)

The information processing apparatus according to any one of (1) to (12) above, in which the recognizing unit is further configured to recognize a translucent zone in a peripheral ooplasm of the fertile ovum and a cell in the fertile ovum, and the feature amount calculating unit is further configured to calculate, as the transformation, change of a proportion of an area of the translucent zone in the peripheral ooplasm to an area of the cell in the fertile ovum.

(14)

The information processing apparatus according to any one of (1) to (13) above, in which the recognizing unit is further configured to recognize a cell in the fertile ovum, and the feature amount calculating unit is further configured to calculate change of a time-series motion amount of the cell in the fertile ovum recognized by the recognizing unit.

(15)

The information processing apparatus according to any one of (1) to (14) above, further including a determining unit configured to determine quality of the fertile ovum on the basis of the feature amount.

(16)

The information processing apparatus according to (15) above, in which the recognizing unit is further configured to recognize a first polar body and a second polar body of the fertile ovum, the feature amount calculating unit is further configured to calculate, as the feature amount, a number of polar bodies of the fertile ovum on the basis of a difference between a sum of an area of the first polar body and an area of the second polar body and the area of the first polar body, and the determining unit is further configured to determine whether or not the polar bodies of the fertile ovum are abnormal on the basis of the number of polar bodies.

(17)

The information processing apparatus according to (15) or (16) above, in which the recognizing unit is further configured to recognize a nucleus of a blastomere of the fertile ovum, the feature amount calculating unit is further configured to calculate, as the feature amount, a number of nuclei on the basis of an area of the nucleus, and the determining unit is further configured to determine whether or not the fertile ovum is in a polynuclear state on the basis of the number of nuclei.

(18)

The information processing apparatus according to any one of (15) to (17) above, in which the determining unit is further configured to determine a growth state of the fertile ovum on the basis of the transformation.

(19)

The information processing apparatus according to any one of (15) to (18) above, in which the recognizing unit is further configured to recognize a zona pellucida of the fertile ovum, the feature amount calculating unit is further configured to calculate, as the transformation, change of a thickness of the zona pellucida, and the determining unit is further configured to determine that the fertile ovum is an expanding blastocyst on the basis of the change of the thickness of the zona pellucida.

(20)

The information processing apparatus according to any one of (15) to (19) above, in which the recognizing unit is further configured to recognize a zona pellucida of the fertile ovum, the feature amount calculating unit is further configured to calculate, as the transformation, at least one of change of a diameter of the zona pellucida and change of an area of the zona pellucida, and the determining unit is further configured to determine that the fertile ovum is an expanding blastocyst on the basis of at least one of the change of the diameter of the zona pellucida and the change of the area of the zona pellucida.

(21)

The information processing apparatus according to any one of (15) to (20) above, in which the recognizing unit is further configured to recognize a pronucleus of the fertile ovum, the feature amount calculating unit is further configured to calculate, as the transformation, change of an area of the pronucleus, and the determining unit is further configured to determine appearance and disappearance of the pronucleus in the fertile ovum on the basis of the change of the area of the pronucleus.

(22)

The information processing apparatus according to (21) above, in which the feature amount calculating unit is further configured to calculate, as the feature amount, a number of pronuclei on the basis of the area of the pronucleus, and the determining unit is further configured to determine whether or not the pronucleus of the fertile ovum is abnormal on the basis of the number of pronuclei.

(23)

The information processing apparatus according to any one of (15) to (22) above, in which the recognizing unit is further configure to recognize a translucent zone in a peripheral ooplasm of the fertile ovum and a cell in the fertile ovum, the feature amount calculating unit is further configured to calculate, as the transformation, change of a proportion of an area of the translucent zone in the peripheral ooplasm to an area of the cell in the fertile ovum, and the determining unit is further configured to determine appearance and disappearance of the translucent zone in the peripheral ooplasm in the fertile ovum on the basis of the change of the proportion.

(24)

The information processing apparatus according to any one of (15) to (23) above, in which the determining unit is further configured to determine a growth state of the fertile ovum on the basis of the time-series change of the motion amount of the cell in the fertile ovum.

(25)

The information processing apparatus according to (24) above, in which the determining unit is further configured to determine that a state of the fertile ovum, in which a total value of motion speed vectors of the cell in the fertile ovum is not less than a first threshold value and change of the motion speed vectors per unit time is approximately zero, is a lag-phase.

(26)

The information processing apparatus according to (24) or (25) above, in which the determining unit is further configured to determine that a state of the fertile ovum, in which a total value of motion speed vectors of the cell in the fertile ovum is more than a first threshold value and change of the motion speed vectors per unit time is not zero, is a degenerative cell proportion of less than 15%.

(27)

The information processing apparatus according to any one of (24) to (26) above, in which the determining unit is further configured to determine that a state of the fertile ovum, in which a total value of motion speed vectors of the cell in the fertile ovum is not more than a first threshold value and change of the motion speed vectors per unit time is approximately zero, is a degenerative cell proportion of not less than 15%.

(28)

The information processing apparatus according to any one of (24) to (27) above, in which the determining unit is further configured to determine that a state of the fertile ovum, in which a motion average speed of the cell in the fertile ovum is greater than a second threshold value, is a degenerative cell proportion of not less than 15% and less than 50%.

(29)

The information processing apparatus according to any one of (24) to (28) above, in which the determining unit is further configured to determine that a state of the fertile ovum, in which a motion average speed of the cell in the fertile ovum is less than a second threshold value, is a degenerative cell proportion of not less than 50%.

(30)

An information processing method, including:

obtaining a plurality of original images of a fertile ovum captured in time series;

generating probability images from the original images, the probability images each representing probability that the fertile ovum is present;

calculating time-series transformation of the fertile ovum from the probability images; and calculating a feature amount of the fertile ovum based on the transformation.

(31)

The information processing method according to (30) above, further including:

generating binarized images from the probability images by processing the probability images by means of a binarizing process with a predetermined threshold value for each pixel;

calculating the time-series transformation of the fertile ovum from the binarized images; and calculating the feature amount of the fertile ovum based on the transformation.

(32)

The information processing method according to (31) above, further including:

generating overlay images by overlaying the binarized images and the original images:

calculating the time-series transformation of the fertile ovum from the overlay images; and calculating the feature amount of the fertile ovum based on the transformation.

(33)

The information processing method according to any one of (30) to (32) above, further including calculating change of a time-series motion amount of the cell in the fertile ovum from the probability images.

(34)

A program, that causes an information processing apparatus to execute the steps of:

obtaining a plurality of original images of a fertile ovum captured in time series;

generating probability images from the original images, the probability images each representing probability that the fertile ovum is present;

calculating time-series transformation of the fertile ovum from the probability images; and calculating a feature amount of the fertile ovum based on the transformation.

(35)

The program according to (34) above, the program causing the information processing apparatus to further execute the steps of:

generating binarized images from the probability images by processing the probability images by means of a binarizing process with a predetermined threshold value for each pixel;

calculating the time-series transformation of the fertile ovum from the binarized images; and calculating the feature amount of the fertile ovum based on the transformation.

(36)

The program according to (35) above, the program causing the information processing apparatus to further execute the steps of:

generating overlay images by overlaying the binarized images and the original images:

calculating the time-series transformation of the fertile ovum from the overlay images; and calculating the feature amount of the fertile ovum based on the transformation.

(37)

The program according to any one of (34) to (36) above, the program causing the information processing apparatus to further execute the steps of calculating change of a time-series motion amount of the cell in the fertile ovum from the probability images.

(38)

An observation system, including:

an image-capture unit configured to capture a plurality of original images of a fertile ovum in time series; and an information processing apparatus including an image obtaining unit configured to obtain the plurality of original images captured by the image-capture unit, a recognizing unit including a probability image generating unit configured to generate probability images from the original images, the probability images each representing probability that the fertile ovum is present, the recognizing unit being configured to recognize the fertile ovum on the basis of the probability images, and a feature amount calculating unit configured to calculate time-series transformation of the fertile ovum from the probability images, and calculate a feature amount of the fertile ovum based on the transformation.

(39)

The observation system according to (38) above, in which the recognizing unit further includes a binarized image generating unit configured to generate binarized images from the probability images by processing the probability images by means of a binarizing process with a predetermined threshold value for each pixel, and is further configured to recognize the fertile ovum on the basis of the binarized images, and the feature amount calculating unit is further configured to calculate the time-series transformation of the fertile ovum from the binarized images, and calculate the feature amount of the fertile ovum based on the transformation.

(40)

The observation system according to (39) above, in which the recognizing unit further includes an overlay image generating unit configured to generate overlay images by overlaying the binarized images and the original images, and is further configured to recognize the fertile ovum on the basis of the overlay images, and the feature amount calculating unit is further configured to calculate the time-series transformation of the fertile ovum from the overlay images, and calculate the feature amount of the fertile ovum based on the transformation.

(41)

The observation system according to any one of (38) to (40) above, in which the recognizing unit is further configured to recognize a cell in the fertile ovum, and the feature amount calculating unit is further configured to calculate change of a time-series motion amount of the cell in the fertile ovum recognized by the recognizing unit.

(42)

An information processing apparatus, including:

an image obtaining unit configured to obtain a plurality of images of a fertile ovum captured in time series;

a recognizing unit including a probability image generating unit configured to generate, for each image of the fertile ovum, a probability image, wherein each position in the probability image represents the probability that at least part of the fertile ovum is present at the corresponding position in the image of the fertile ovum; and a feature amount calculating unit configured to calculate time-series transformation of the fertile ovum from the probability images over the time series, and calculate a feature amount of the fertile ovum based on the transformation.

(43)

The information processing apparatus according to (42), wherein the recognizing unit further includes a binarized image generating unit configured to generate a plurality of binarized images from a plurality of the probability images by processing the probability images by means of a binarizing process with a predetermined threshold value for each pixel, and is further configured to recognize the fertile ovum on the basis of the binarized images, and the feature amount calculating unit is further configured to calculate the time-series transformation of the fertile ovum from the binarized images, and calculate the feature amount of the fertile ovum based on the transformation.

(44)

The information processing apparatus according to (43), wherein the recognizing unit further includes an overlay image generating unit configured to generates overlay images by overlaying the binarized images and the images of the fertile ovum, and is further configured to recognize the fertile ovum on the basis of the overlay images, and the feature amount calculating unit is further configured to calculate the time-series transformation of the fertile ovum from the overlay images, and calculate the feature amount of the fertile ovum based on the transformation.

(45)

The information processing apparatus according to (42), wherein the recognizing unit is further configured to recognize a zona pellucida of the fertile ovum and a cell in the fertile ovum, and the feature amount calculating unit is further configured to calculate, as the transformation, change of an area of the zona pellucida and change of an area of the cell in the fertile ovum.

(46)

The information processing apparatus according to (45), wherein the feature amount calculating unit is further configured to calculate, as the feature amount, at least one of compaction time of the fertile ovum and cleavage time of the fertile ovum on the basis of time-series change of the area of the zona pellucida and time-series change of the area of the cell in the fertile ovum.

(47)

The information processing apparatus according to (45), wherein the recognizing unit is further configured to recognize a blastocyst as the cell in the fertile ovum, and the feature amount calculating unit is further configured to calculate, as the feature amount, at least one of a number of times of contraction, a contraction diameter, contraction speed, a contraction time period, contraction intervals, contraction strength, contraction frequency, a number of times of dilation, a dilation diameter, a dilation speed, a dilation time period, dilation intervals, dilation strength, and dilation frequency of the zona pellucida and the blastocyst on the basis of time-series change of a difference between the area of the zona pellucida and an area of the blastocyst.

(48)

The information processing apparatus according to (42), wherein the recognizing unit is further configured to recognize a zona pellucida of the fertile ovum, and the feature amount calculating unit is further configured to calculate, as the transformation, a change of a physiological characteristic of the zona pellucida.

(49)

The information processing apparatus according to (48), wherein the physiological characteristic is at least one of a diameter, an area, and a thickness of the zona pellucida.

(50)

The information processing apparatus according to (42), wherein the recognizing unit is further configured to recognize a pronucleus of the fertile ovum, and the feature amount calculating unit is further configured to calculate, as the transformation, a change of an area of the pronucleus.

(51)

The information processing apparatus according to (50, wherein the feature amount calculating unit is further configured to calculate, as the feature amount, a number of pronuclei on the basis of the area of the pronucleus.

(52)

The information processing apparatus according to (42), wherein the recognizing unit is further configured to recognize a first polar body and a second polar body of the fertile ovum, and the feature amount calculating unit is further configured to calculate, as the feature amount, a number of polar bodies of the fertile ovum on the basis of a difference between a sum of an area of the first polar body and an area of the second polar body and the area of the first polar body.

(53)

The information processing apparatus according to (42), wherein the recognizing unit is further configured to recognize a nucleus of a blastomere of the fertile ovum, and the feature amount calculating unit is further configured to calculate, as the feature amount, a number of nuclei on the basis of an area of the nucleus.

(54)

The information processing apparatus according to (42), wherein the recognizing unit is further configured to recognize a zona pellucida of the fertile ovum, a cell in the fertile ovum, and fragmentation of the fertile ovum, and the feature amount calculating unit is further configured to calculate, as the feature amount, a proportion of an area of the fragmentation to a sum of an area of the zona pellucida and an area of the cell in the fertile ovum.

(55)

The information processing apparatus according to (42), wherein the recognizing unit is further configured to recognize a translucent zone in a peripheral ooplasm of the fertile ovum and a cell in the fertile ovum, and the feature amount calculating unit is further configured to calculate, as the transformation, a change of a proportion of an area of the translucent zone in the peripheral ooplasm to an area of the cell in the fertile ovum.

(56)

The information processing apparatus according to (42), wherein the recognizing unit is further configured to recognize a cell in the fertile ovum, and the feature amount calculating unit is further configured to calculate change of a time-series motion amount of the cell in the fertile ovum recognized by the recognizing unit.

(57)

The information processing apparatus according to (56), further comprising a determining unit configured to determine quality of the fertile ovum on the basis of the feature amount.

(58)

The information processing apparatus according to (57), wherein the recognizing unit is further configured to recognize a first polar body and a second polar body of the fertile ovum, the feature amount calculating unit is further configured to calculate, as the feature amount, a number of polar bodies of the fertile ovum on the basis of a difference between a sum of an area of the first polar body and an area of the second polar body and the area of the first polar body, and the determining unit is further configured to determine whether or not the polar bodies of the fertile ovum are abnormal on the basis of the number of polar bodies.

(59)

The information processing apparatus according to (57), wherein the recognizing unit is further configured to recognize a nucleus of a blastomere of the fertile ovum, the feature amount calculating unit is further configured to calculate, as the feature amount, a number of nuclei on the basis of an area of the nucleus, and the determining unit is further configured to determine whether or not the fertile ovum is in a polynuclear state on the basis of the number of nuclei.

(60)

The information processing apparatus according to (57), wherein the determining unit is further configured to determine a growth state of the fertile ovum on the basis of the transformation.

(61)

The information processing apparatus according to (60), wherein the recognizing unit is further configured to recognize a zona pellucida of the fertile ovum, the feature amount calculating unit is further configured to calculate, as the transformation, a change of a thickness of the zona pellucida, and the determining unit is further configured to determine that the fertile ovum is an expanding blastocyst on the basis of the change of the thickness of the zona pellucida.

(62)

The information processing apparatus according to (60), wherein the recognizing unit is further configured to recognize a zona pellucida of the fertile ovum, the feature amount calculating unit is further configured to calculate, as the transformation, at least one of change of a diameter of the zona pellucida and change of an area of the zona pellucida, and the determining unit is further configured to determine that the fertile ovum is an expanding blastocyst on the basis of at least one of the change of the diameter of the zona pellucida and the change of the area of the zona pellucida.

(63)

The information processing apparatus according to (60), wherein the recognizing unit is further configured to recognize a pronucleus of the fertile ovum, the feature amount calculating unit is further configured to calculate, as the transformation, a change of an area of the pronucleus, and the determining unit is further configured to determine appearance and disappearance of the pronucleus in the fertile ovum on the basis of the change of the area of the pronucleus.

(64)

The information processing apparatus according to (63), wherein the feature amount calculating unit is further configured to calculate, as the feature amount, a number of pronuclei on the basis of the area of the pronucleus, and the determining unit is further configured to determine whether or not the pronucleus of the fertile ovum is abnormal on the basis of the number of pronuclei.

(65)

The information processing apparatus according to (60), wherein the recognizing unit is further configure to recognize a translucent zone in a peripheral ooplasm of the fertile ovum and a cell in the fertile ovum, the feature amount calculating unit is further configured to calculate, as the transformation, a change of a proportion of an area of the translucent zone in the peripheral ooplasm to an area of the cell in the fertile ovum, and the determining unit is further configured to determine appearance and disappearance of the translucent zone in the peripheral ooplasm in the fertile ovum on the basis of the change of the proportion.

(66)

The information processing apparatus according to (57), wherein the determining unit is further configured to determine a growth state of the fertile ovum on the basis of the time-series change of the motion amount of the cell in the fertile ovum.

(67)

The information processing apparatus according to (66), wherein the determining unit is further configured to determine that a state of the fertile ovum, in which a total value of motion speed vectors of the cell in the fertile ovum is not less than a first threshold value and change of the motion speed vectors per unit time is approximately zero, is a lag-phase.

(68)

The information processing apparatus according to (67), wherein the determining unit is further configured to determine that a state of the fertile ovum, in which a total value of motion speed vectors of the cell in the fertile ovum is more than a first threshold value and change of the motion speed vectors per unit time is not zero, is a degenerative cell proportion of less than 15%.

(69)

The information processing apparatus according to (66), wherein the determining unit is further configured to determine that a state of the fertile ovum, in which a total value of motion speed vectors of the cell in the fertile ovum is not more than a first threshold value and change of the motion speed vectors per unit time is approximately zero, is a degenerative cell proportion of not less than 15%.

(70)

The information processing apparatus according to (69), wherein the determining unit is further configured to determine that a state of the fertile ovum, in which a motion average speed of the cell in the fertile ovum is greater than a second threshold value, is a degenerative cell proportion of not less than 15% and less than 50%.

(71)

The information processing apparatus according to (69), wherein the determining unit is further configured to determine that a state of the fertile ovum, in which a motion average speed of the cell in the fertile ovum is less than a second threshold value, is a degenerative cell proportion of not less than 50%.

(72)

The information processing apparatus according to (42), wherein the position in the image of the fertile ovum is a pixel position.

(73)

An information processing method, including:

obtaining a plurality of images of a fertile ovum captured in time series;

generating, for each image of the fertile ovum, a probability image, wherein each position in the probability image represents the probability that at least part of the fertile ovum is present at the corresponding position in the image of the fertile ovum;

calculating time-series transformation of the fertile ovum from the probability images over the time series, and calculating a feature amount of the fertile ovum based on the transformation.

(74)

A program, that causes an information processing apparatus to execute the steps of:

obtaining a plurality of original images of a fertile ovum captured in time series;

generating, for each image of the fertile ovum, a probability image, wherein each position in the probability image represents the probability that at least part of the fertile ovum is present at the corresponding position in the image of the fertile ovum;

calculating time-series transformation of the fertile ovum from the probability images over the time series, and calculating a feature amount of the fertile ovum based on the transformation.

(75)

An observation system, including:

an image-capture unit configured to capture a plurality of images of a fertile ovum in time series; and an information processing apparatus including an image obtaining unit configured to obtain the plurality of images captured by the image-capture unit, a recognizing unit including a probability image generating unit configured to generate, for each image of the fertile ovum, a probability image, wherein each position in the probability image represents the probability that at least part of the fertile ovum is present at the corresponding position in the image of the fertile ovum; and a feature amount calculating unit configured to calculate time-series transformation of the fertile ovum from the probability images over the time series, and calculate a feature amount of the fertile ovum based on the transformation.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST

100 observation system
10 incubator
20 observation device
21 image-capture unit
22 light source
23 culture dish group
23a culture dish
30 humidity-temperature-gas controller unit
40 detector unit
50 information processing apparatus
51 image obtaining unit
52 image processing unit
53 recognizing unit
54 feature amount calculating unit
55 image-capture controller unit
56 determining unit
57 predicting unit
58 display controller unit
59 fertile ovum information database
60 display device
70 input unit
F fertile ovum
W well

The invention claimed is:

1. An information processing apparatus, comprising:
circuitry configured to function as:
an image obtaining unit configured to obtain a plurality of images of a fertile ovum captured in time series;
a recognizing unit including a probability image generating unit configured to generate, for each image of the fertile ovum, a probability image, wherein each position in the probability image represents the probability that at least part of the fertile ovum is present at the corresponding position in the image of the fertile ovum; and
a feature amount calculating unit configured to
calculate time-series transformation of the fertile ovum from the probability images over the time series, and
calculate a feature amount of the fertile ovum based on the transformation, wherein the recognizing unit is further configured to recognize a translucent zone in a peripheral ooplasm of the fertile ovum and a cell in the fertile ovum, and the feature amount calculating unit is further configured to calculate, as the transformation, a change of a proportion of an area of the translucent zone in the peripheral ooplasm to an area of the cell in the fertile ovum.

2. The information processing apparatus according to claim 1, wherein the recognizing unit further includes a binarized image generating unit configured to generate a plurality of binarized images from a plurality of the probability images by processing the probability images by means of a binarizing process with a predetermined threshold value for each pixel, and is further configured to recognize the fertile ovum on the basis of the binarized images, and the feature amount calculating unit is further configured to calculate the time-series transformation of the fertile ovum from the binarized images, and calculate the feature amount of the fertile ovum based on the transformation.

3. The information processing apparatus according to claim 2, wherein the recognizing unit further includes an overlay image generating unit configured to generates overlay images by overlaying the binarized images and the images of the fertile ovum, and is further configured to recognize the fertile ovum on the basis of the overlay images, and the feature amount calculating unit is further configured to calculate the time-series transformation of the fertile ovum from the overlay images, and calculate the feature amount of the fertile ovum based on the transformation.

4. The information processing apparatus according to claim 1, wherein the recognizing unit is further configured to recognize a zona pellucida of the fertile ovum and a cell in the fertile ovum, and the feature amount calculating unit is further configured to calculate, as the transformation, change of an area of the zona pellucida and change of an area of the cell in the fertile ovum.

5. The information processing apparatus according to claim 4, wherein the feature amount calculating unit is further configured to calculate, as the feature amount, at least one of compaction time of the fertile ovum and cleavage time of the fertile ovum on the basis of time-series change of the area of the zona pellucida and time-series change of the area of the cell in the fertile ovum.

6. The information processing apparatus according to claim 4, wherein the recognizing unit is further configured to recognize a blastocyst as the cell in the fertile ovum, and the feature amount calculating unit is further configured to calculate, as the feature amount, at least one of a number of times of contraction, a contraction diameter, contraction speed, a contraction time period, contraction intervals, contraction strength, contraction frequency, a number of times of dilation, a dilation diameter, a dilation speed, a dilation time period, dilation intervals, dilation strength, and dilation frequency of the zona pellucida and the blastocyst on the basis of time-series change of a difference between the area of the zona pellucida and an area of the blastocyst.

7. The information processing apparatus according to claim 1, wherein the recognizing unit is further configured to recognize a zona pellucida of the fertile ovum, and the feature amount calculating unit is further configured to calculate, as the transformation, a change of a physiological characteristic of the zona pellucida.

8. The information processing apparatus according to claim 7, wherein the physiological characteristic is at least one of a diameter, an area, and a thickness of the zona pellucida.

9. The information processing apparatus according to claim 1, wherein the recognizing unit is further configured to recognize a pronucleus of the fertile ovum, and the feature amount calculating unit is further configured to calculate, as the transformation, a change of an area of the pronucleus.

10. The information processing apparatus according to claim 9, wherein the feature amount calculating unit is further configured to calculate, as the feature amount, a number of pronuclei on the basis of the area of the pronucleus.

11. The information processing apparatus according to claim 1, wherein the recognizing unit is further configured to recognize a first polar body and a second polar body of the fertile ovum, and the feature amount calculating unit is further configured to calculate, as the feature amount, a number of polar bodies of the fertile ovum on the basis of a difference between a sum of an area of the first polar body and an area of the second polar body and the area of the first polar body.

12. The information processing apparatus according to claim 1, wherein the recognizing unit is further configured to recognize a nucleus of a blastomere of the fertile ovum, and the feature amount calculating unit is further configured to calculate, as the feature amount, a number of nuclei on the basis of an area of the nucleus.

13. The information processing apparatus according to claim 1, wherein the recognizing unit is further configured to recognize a zona pellucida of the fertile ovum, a cell in the fertile ovum, and fragmentation of the fertile ovum, and the feature amount calculating unit is further configured to calculate, as the feature amount, a proportion of an area of the fragmentation to a sum of an area of the zona pellucida and an area of the cell in the fertile ovum.

14. The information processing apparatus according to claim 1, wherein the recognizing unit is further configured to recognize a cell in the fertile ovum, and the feature amount calculating unit is further configured to calculate change of a time-series motion amount of the cell in the fertile ovum recognized by the recognizing unit.

15. The information processing apparatus according to claim 14, further comprising a determining unit configured to determine quality of the fertile ovum on the basis of the feature amount.

16. The information processing apparatus according to claim 15, wherein the recognizing unit is further configured to recognize a first polar body and a second polar body of the fertile ovum, the feature amount calculating unit is further configured to calculate, as the feature amount, a number of polar bodies of the fertile ovum on the basis of a difference between a sum of an area of the first polar body and an area of the second polar body and the area of the first polar body, and the determining unit is further configured to determine whether or not the polar bodies of the fertile ovum are abnormal on the basis of the number of polar bodies.

17. The information processing apparatus according to claim 15, wherein the recognizing unit is further configured to recognize a nucleus of a blastomere of the fertile ovum, the feature amount calculating unit is further configured to calculate, as the feature amount, a number of nuclei on the basis of an area of the nucleus, and the determining unit is further configured to determine whether or not the fertile ovum is in a polynuclear state on the basis of the number of nuclei.

18. The information processing apparatus according to claim 15, wherein the determining unit is further configured to determine a growth state of the fertile ovum on the basis of the transformation.

19. The information processing apparatus according to claim 18, wherein the recognizing unit is further configured to recognize a zona pellucida of the fertile ovum, the feature amount calculating unit is further configured to calculate, as the transformation, a change of a thickness of the zona pellucida, and the determining unit is further configured to determine that the fertile ovum is an expanding blastocyst on the basis of the change of the thickness of the zona pellucida.

20. The information processing apparatus according to claim 18, wherein the recognizing unit is further configured to recognize a zona pellucida of the fertile ovum, the feature amount calculating unit is further configured to calculate, as the transformation, at least one of change of a diameter of the zona pellucida and change of an area of the zona pellucida, and the determining unit is further configured to determine that the fertile ovum is an expanding blastocyst on the basis of at least one of the change of the diameter of the zona pellucida and the change of the area of the zona pellucida.

21. The information processing apparatus according to claim 18, wherein the recognizing unit is further configured to recognize a pronucleus of the fertile ovum, the feature amount calculating unit is further configured to calculate, as the transformation, a change of an area of the pronucleus, and the determining unit is further configured to determine appearance and disappearance of the pronucleus in the fertile ovum on the basis of the change of the area of the pronucleus.

22. The information processing apparatus according to claim 21, wherein the feature amount calculating unit is further configured to calculate, as the feature amount, a number of pronuclei on the basis of the area of the pronucleus, and the determining unit is further configured to determine whether or not the pronucleus of the fertile ovum is abnormal on the basis of the number of pronuclei.

23. The information processing apparatus according to claim 18, wherein the recognizing unit is further configure to recognize a translucent zone in a peripheral ooplasm of the fertile ovum and a cell in the fertile ovum, the feature amount calculating unit is further configured to calculate, as the transformation, a change of a proportion of an area of the translucent zone in the peripheral ooplasm to an area of the cell in the fertile ovum, and the determining unit is further configured to determine appearance and disappearance of the translucent zone in the peripheral ooplasm in the fertile ovum on the basis of the change of the proportion.

24. The information processing apparatus according to claim 15, wherein the determining unit is further configured to determine a growth state of the fertile ovum on the basis of the time-series change of the motion amount of the cell in the fertile ovum.

25. The information processing apparatus according to claim 24, wherein the determining unit is further configured to determine that a state of the fertile ovum, in which a total value of motion speed vectors of the cell in the fertile ovum is not less than a first threshold value and change of the motion speed vectors per unit time is approximately zero, is a lag-phase.

26. The information processing apparatus according to claim 24, wherein the determining unit is further configured to determine that a state of the fertile ovum, in which a total value of motion speed vectors of the cell in the fertile ovum is more than a first threshold value and change of the motion speed vectors per unit time is not zero, is a degenerative cell proportion of less than 15%.

27. The information processing apparatus according to claim 24, wherein the determining unit is further configured to determine that a state of the fertile ovum, in which a total value of motion speed vectors of the cell in the fertile ovum is not more than a first threshold value and change of the motion speed vectors per unit time is approximately zero, is a degenerative cell proportion of not less than 15%.

28. The information processing apparatus according to claim 27, wherein the determining unit is further configured to determine that a state of the fertile ovum, in which a motion average speed of the cell in the fertile ovum is greater than a second threshold value, is a degenerative cell proportion of not less than 15% and less than 50%.

29. The information processing apparatus according to claim 27, wherein the determining unit is further configured to determine that a state of the fertile ovum, in which a motion average speed of the cell in the fertile ovum is less than a second threshold value, is a degenerative cell proportion of not less than 50%.

30. The information processing apparatus according to claim 1, wherein the position in the image of the fertile ovum is a pixel position.

31. An information processing method, comprising:

obtaining a plurality of images of a fertile ovum captured in time series;

generating, for each image of the fertile ovum, a probability image, wherein each position in the probability image represents the probability that at least part of the fertile ovum is present at the corresponding position in the image of the fertile ovum;

calculating time-series transformation of the fertile ovum from the probability images over the time series;

calculating a feature amount of the fertile ovum based on the transformation;

recognizing a translucent zone in a peripheral ooplasm of the fertile ovum and a cell in the fertile ovum; and calculating, as the transformation, a change of a proportion of an area of the translucent zone in the peripheral ooplasm to an area of the cell in the fertile ovum.

32. A non-transitory storage medium encoded with instructions that, when executed by a computer, execute processing comprising:

obtaining a plurality of original images of a fertile ovum captured in time series;

generating, for each image of the fertile ovum, a probability image, wherein each position in the probability image represents the probability that at least part of the fertile ovum is present at the corresponding position in the image of the fertile ovum;

calculating time-series transformation of the fertile ovum from the probability images over the time series;

calculating a feature amount of the fertile ovum based on the transformation;

recognizing a translucent zone in a peripheral ooplasm of the fertile ovum and a cell in the fertile ovum; and calculating, as the transformation, a change of a proportion of an area of the translucent zone in the peripheral ooplasm to an area of the cell in the fertile ovum.

33. An observation system, comprising:

circuitry configured to function as:

an image-capture unit configured to capture a plurality of images of a fertile ovum in time series; and an information processing apparatus including an image obtaining unit configured to obtain the plurality of images captured by the image-capture unit, a recognizing unit including a probability image generating unit configured to generate, for each image of the fertile ovum, a probability image, wherein each position in the probability image represents the probability that at least part of the fertile ovum is present at the corresponding position in the image of the fertile ovum; and a feature amount calculating unit configured to calculate time-series transformation of the fertile ovum from the probability images over the time series, and calculate a feature amount of the fertile ovum based on the transformation, wherein the recognizing unit is further configured to recognize a translucent zone in a peripheral ooplasm of the fertile ovum and a cell in the fertile ovum, and the feature amount calculating unit is further configured to calculate, as the transformation, a change of a proportion of an area of the translucent zone in the peripheral ooplasm to an area of the cell in the fertile ovum.

* * * * *